United States Patent [19]

Kehne et al.

[11] Patent Number: 5,102,443

[45] Date of Patent: Apr. 7, 1992

[54] HETEROCYCLICALLY SUBSTITUTED PHENOXYSULFONYLUREAS, AND THE USE THEREOF AS HERBICIDES OR PLANT GROWTH REGULATORS

[75] Inventors: Heinz Kehne, Hofheim am Taunus; Lothar Willms, Hillscheid; Klaus Bauer, Hanauein/Taunus; Hermann Bieringer, Eppstein/Taunus; Helmut Bürstell, Frankfurt am Main, all of Fed. Rep. of Germany

[73] Assignee: Hoechst Aktiengesellschaft, Frankfurt, Fed. Rep. of Germany

[21] Appl. No.: 351,958

[22] Filed: May 15, 1989

[30] Foreign Application Priority Data

May 17, 1988 [DE] Fed. Rep. of Germany ....... 3816703

[51] Int. Cl.⁵ .................. A01N 43/54; C07D 239/42; C07D 239/26; C07D 239/69
[52] U.S. Cl. ......................... 71/92; 544/321; 544/324; 544/323; 544/327; 544/331; 544/332; 544/333; 544/334; 544/335
[58] Field of Search .................. 71/92; 544/321, 324, 544/323, 327, 331, 332, 333, 334, 335

[56] References Cited

U.S. PATENT DOCUMENTS

| | | | |
|---|---|---|---|
| 4,394,153 | 7/1983 | Reap | 71/92 |
| 4,581,059 | 4/1986 | Adams et al. | 71/92 |
| 4,678,500 | 7/1987 | Hay et al. | 71/92 |

FOREIGN PATENT DOCUMENTS 62-277306 2/1987 Japan.
62-155202 10/1987 Japan.

OTHER PUBLICATIONS

Kato et al., Chemical Abstracts 108:200229s (1988).
Kato et al., Chemical Abstracts 108:33622f (1988).

*Primary Examiner*—John M. Ford
*Attorney, Agent, or Firm*—Curtis, Morris & Safford, P.C.

[57] ABSTRACT

Heterocyclically substituted phenoxysulfonylureas, processes for the preparation thereof, and the use thereof as herbicides or plant growth regulators. Compounds of the formula I or the salts thereof

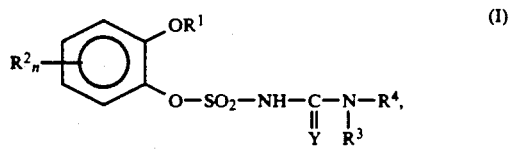

where
$R^1$ is $(C_1-C_8)$alkyl, $(C_2-C_8)$alkenyl or $(C_2-C_8)$alkynyl, these radicals being substituted by halogen, saturated or unsaturated $(C_1-C_6)$alkoxy, $(C_1-C_6)$alkylthio, -sulfinyl or -sulfonyl, $(C_1-C_6)$alkoxycarbonyl, $NO_2$, $CN$ or phenyl; furthermore is $(C_2-C_8)$alkenyl, $(C_2-C_8)$alkynyl or $(C_3-C_8)$cycloalkyl, which can be substituted by halogen or by alkoxy or alkylthio; $(C_5-C_8)$cycloalkenyl, cyclopropylmethyl, epoxypropyl, furfuryl, tetrahydrofurfuryl or phenoxy $(C_1-C_4)$alkyl, it being possible for the last three substituents mentioned to be substituted by halogen, alkyl or alkoxy; or phenyl which can be substituted by halogen, alkyl, alkoxy, $NO_2$, $CF_3$, $CN$ or $OCHF_2$; or, in the event that $R^2$ is alkenyl, alkynyl, phenyl or phenoxy, each of which can be substituted as indicated below, alkylsulfonyl or alkylsulfinyl and $n \neq$, $R^1$ is also $(C_1-C_8)$alkyl,
$R^2$ radicals independently of one another are $(C_1-C_8)$-alkyl, $(C_2-C_8)$alkenyl, $(C_2-C_8)$alkynyl, phenyl, phenoxy, $(C_1-C_4)$alkoxy, $(C_1-C_4)$alkylthio, $(C_1-C_4)$-alkoxycarbonyl, $(C_2-C_4)$alkenyloxycarbonyl, $(C_2-C_4)$alkynyloxycarbonyl, it being possible for all the abovementioned radicals to be substituted by halogen, $(C_1-C_4)$alkoxy or $(C_1-C_4)$alkylthio; furthermore halogen, $NO_2$, $(C_1-C_4)$alkylsulfonyl or $(C_1-C_4)$alkylsulfinyl;
n is 0, 1, 2 or 3; y is O or S;
$R^3$ is hydrogen, $(C_1-C_8)$alkyl, $(C_2-C_8)$alkenyl, $(C_3-C_8)$-alkynyl or $(C_1-C_4)$alkoxy;
$R^4$ is a heterocyclic radical of the formulae

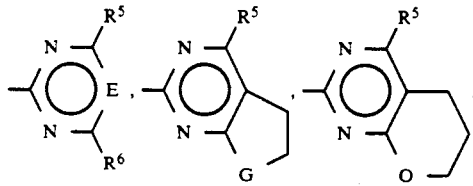

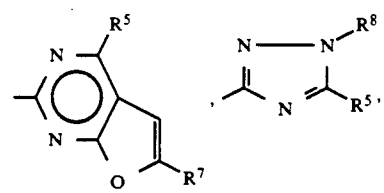

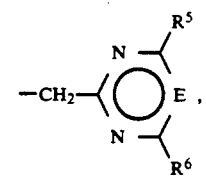

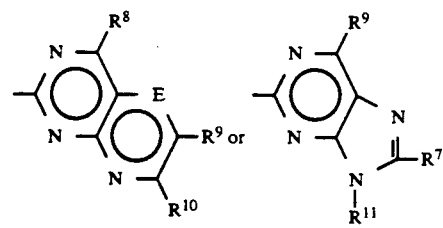

E is CH or N,
G is O or CH₂, (Abstract continued a next page.)

$R^5$ and $R^6$ are hydrogen, halogen, alkyl, alkoxy or alkylthio, it being possible for the abovementioned alkyl-containing radicals to be substituted by halogen, alkoxy or alkylthio, furthermore a radical of the formula $-NR^{12}R^{13}$, $-OCHR^7-CO_2R^{12}$, cycloalkyl, alkenyl, alkynyl, alkenyloxy or alkynyloxy, $R^7$ is hydrogen or alkyl; $R^8$ is alkyl, $-CHF_2$ or $-CH_2CF$;

$R^9$ and $R^{10}$ are hydrogen, alkyl, alkoxy or halogen, $R^{11}$ is hydrogen, alkyl, $-CHF_2$ or $CH_2CF_3$, and $R^{12}$ and $R^{13}$ are hydrogen, alkyl, alkenyl or alkynyl, have outstanding herbicidal and plant growth-regulating properties.

16 Claims, No Drawings

HETEROCYCLICALLY SUBSTITUTED PHENOXYSULFONYLUREAS, AND THE USE THEREOF AS HERBICIDES OR PLANT GROWTH REGULATORS

It is known that heterocyclically substituted phenoxysulfonylureas possess herbicidal and plant-growth regulating properties (EP-A 4,163, EP-A 113,956, DE-A 3,151-450).

It has now been found that heterocyclically substituted sulfamic acid phenyl esters, the phenyl ester moiety of which is formed by specific pyrocatechol monoethers, are particularly suitable as herbicides and plant growth regulators.

The present invention therefore relates to compounds of the formula (I) or salts thereof

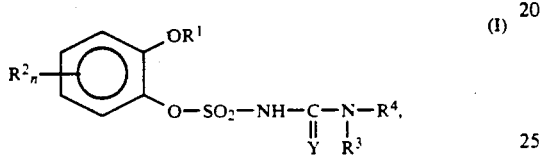

where $R^1$ is $(C_1-C_8)$alkyl, $(C_2-C_8)$alkenyl, $(C_2-C_8)$alkynyl, each of these radicals being monosubstituted or polysubstituted by halogen or monosubstituted or disubstituted by $(C_1-C_6)$alkoxy, $(C_2-C_6)$alkenyloxy, $(C_2-C_6)$-alkynyloxy, $(C_1-C_6)$alkylthio, $(C_1-C_6)$alkylsulfinyl, $(C_1-C_6)$alkylsulfonyl, $(C_1-C_6)$alkoxycarbonyl, $NO_2$, CN or by phenyl; furthermore $(C_2-C_8)$alkenyl, $(C_2-C_8)$-alkynyl, $(C_3-C_8)$cycloalkyl, which can be monosubstituted or polysubstituted by halogen or monosubstituted or disubstituted by $(C_1-C_4)$alkoxy or $(C_1-C_4)$alkylthio; $(C_5-C_8)$cycloalkenyl, cyclopropylmethyl, epoxypropyl; furfuryl, tetrahydrofurfuryl, phenoxy $(C_1-C_4)$alkyl, it being possible for the last three substituents mentioned to be substituted by halogen, $(C_1-C_4)$alkyl or $(C_1-C_4)$alkoxy; or phenyl which can be monosubstituted or polysubstituted by halogen, $(C_1-C_4)$alkyl, $(C_1-C_4)$alkoxy, $NO_2$, $CF_3$, CN or $OCHF_2$; or in the event that $R^2$ is $(C_2-C_8)$alkenyl, $(C_2-C_8)$-alkynyl, phenyl, phenoxy, each of which can be substituted as indicated below, $(C_1-C_4)$alkylsulfonyl or $(C_1-C_4)$alkylsulfinyl and $n\neq 0$, $R^1$ is also $(C_1-C_8)$alkyl, $R^2$ radicals independently of one another are $(C_1-C_8)$-alkyl, $(C_2-C_8)$alkenyl, $(C_2-C_8)$alkynyl, phenyl, phenoxy, $(C_1-C_4)$alkoxy, $(C_1-C_4)$alkylthio, $(C_1-C_4)$alkoxycarbonyl, $(C_2-C_4)$alkenyloxycarbonyl or $(C_2-C_4)$alkynyloxycarbonyl, it being possible for all of the abovementioned radicals to be monosubstituted or polysubstituted by halogen or monosubstituted to disubstituted by $(C_1-C_4)$alkoxy or $(C_1-C_4)$alkylthio; furthermore are halogen, $NO_2$, $(C_1-C_4)$alkylsulfonyl or $(C_1-C_4)$alkylsulfinyl;

n is 0, 1, 2 or 3;

Y is O or S;

$R^3$ is hydrogen, $(C_1-C_8)$alkyl, $(C_2-C_8)$alkenyl, $(C_3-C_8)$-alkynyl or $(C_1-C_4)$alkoxy;

$R^4$ is a heterocyclic radical of the formulae

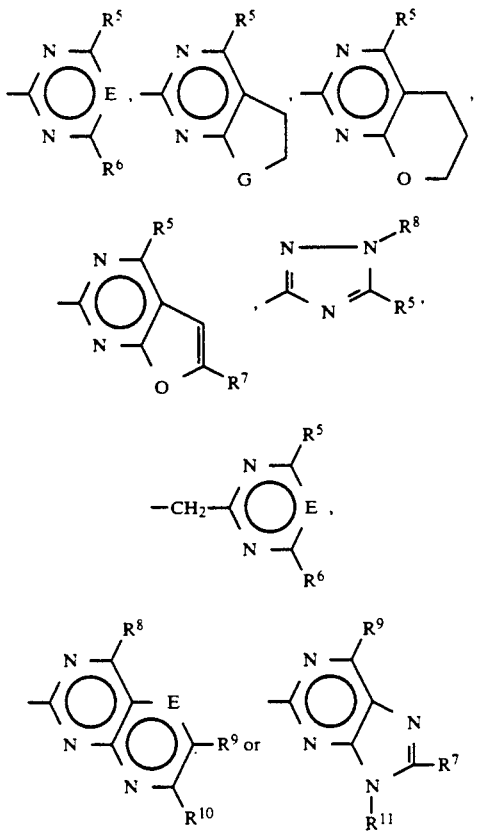

E is CH or N,

G is O or $CH_2$, $R^5$ and $R^6$ independently of one another are hydrogen, halogen, $(C_1-C_6)$ alkyl, $(C_1-C_6)$ alkoxy or $(C_1-C_6)$ alkylthio, it being possible for the abovementioned alkyl-containing radicals to be monosubstituted or polysubstituted by halogen or monosubstituted or disubstituted by $(C_1-C_4)$ alkoxy or $(C_1-C_4)$alkylthio, furthermore are a radical of the formula $-NR^{12}R^{13}$, $-OCHR^7-CO_2R^{12}$, $(C_3-C_6)$cycloalkyl, $(C_3-C_5)$alkenyl, $(C_2-C_4)$alkynyl, $(C_3-C_5)$alkenyloxy, or $(C_3-C_5)$alkynyloxy, $R^7$ is hydrogen or $(C_1-C_4)$alkyl, $R^8$ is $(C_1-C_4)$alkyl, $-CHF_2$ or $-CH_2CF_3$, $R^9$ and $R^{10}$ independently of one another are hydrogen, $(C_1-C_4)$alkyl, $(C_1-C_5)$alkoxy or halogen, $R^{11}$ is hydrogen, $(C_1-C_4)$alkyl, $-CHF_2$ or $CH_2CF_3$ and $R^{12}$ and $R^{13}$ independently of one another are hydrogen, $(C_1-C_4)$alkyl, $(C_2-C_4)$alkenyl or $(C_3-C_4)$alkynyl.

The compounds of the formula (I) can form salts in which the hydrogen of the $-SO_2-NH-$ group is replaced by a cation which is suitable for agriculture. In general, these salts are metal salts, in particular alkali metal salts, alkaline earth metal salts, optionally alkylated ammonium salts or organic amine salts.

Preferred compounds of the formula (I) and salts thereof are those in which $R^1$ is $(C_1-C_4)$alkyl, $(C_2-C_5)$alkenyl or $(C_2-C_4)$alkynyl, these radicals being substituted as described above; furthermore is $(C_2-C_5)$alkenyl, $(C_2-C_4)$alkynyl or, in the event that $n=1$ and $R^2$ is $(C_2-C_8)$alkenyl or $(C_2-C_8)$alkynyl, is $(C_1-C_4)$alkyl; $R^2$ is $(C_1-C_4)$alkyl, $(C_2-C_5)$alkenyl, $(C_2-C_4)$alkynyl, $(C_1-C_4$ )alkoxycarbonyl, phenyl, phenoxy, ($C_1$-$C_4$)alkoxy or ($C_1$-$C_4$)alkylthio, it being possible for these radicals to be substituted as described above; or is halogen; n is 0, 1 or 2, Y is O, $R^3$ is hydrogen, ($C_1$-$C_4$)alkyl or ($C_3$-$C_4$)alkenyl, $R^4$ is a heterocyclic radical of the formula

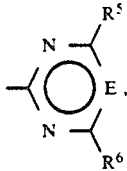

E is CH or N, $R^5$ and $R^6$ independently of one another are halogen, ($C_1$-$C_4$)alkyl, ($C_1$-$C_4$)alkoxy or ($C_1$-$C_4$)alkylthio, each of which can be substituted as described above.

Halogen is preferably fluorine, chlorine or bromine.

Particularly preferred compounds of the formula (I) and salts thereof are those where $R^1$ is ($C_1$-$C_4$)alkyl, ($C_2$-$C_5$)alkenyl or ($C_2$-$C_4$)alkynyl, these radicals being substituted as described above, furthermore ($C_2$-$C_5$)alkenyl or ($C_2$-$C_4$)alkynyl; $R^2$ is ($C_1$-$C_4$)alkyl, ($C_2$-$C_5$)alkenyl, ($C_1$-$C_4$)alkoxycarbonyl, ($C_1$-$C_4$)alkoxy, ($C_1$-$C_4$)alkylthio, each of which can be substituted as described above; or is fluorine or chlorine, n=0 or 1, $R^3$ is hydrogen or methyl, $R^4$ is a heterocyclic radical of the formula

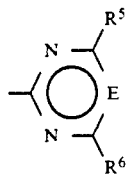

E is CH or N and $R^5$ and $R^6$ independently of one another are chlorine, bromine, ($C_1$-$C_4$)alkyl, ($C_1$-$C_4$)alkoxy, $OCHF_2$, $OCH_2CF_3$ or $CF_3$.

The present invention also relates to processes for the preparation of compounds of the general formula (I) or salts thereof, characterized in that (a) a compound of the formula (II)

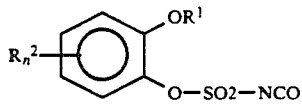

is reacted with a compound of the formula (III)

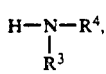

or (b) a compound of the formula (IV)

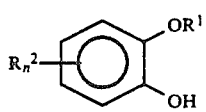

is reacted with a chlorosulfonylurea of the formula (V)

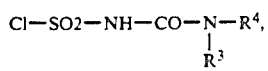

or (c) a compound of the formula (VI)

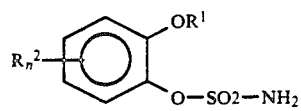

is reacted with a carbamate of the formula (VII)

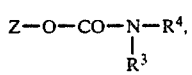

where Z is phenyl or ($C_1$-$C_6$)alkyl, and, if desired, the resulting compounds of the formula I are converted into their salts.

The compounds of the formulae (II) and (III) are preferably reacted in inert aprotic solvents, such as, for example, acetonitrile, dichloromethane, toluene, tetrahydrofuran or dioxane, at temperatures between 0° C. and the boiling point of the solvent.

The phenoxysulfonyl isocyanates of the formula (II) can be prepared in a simple manner by processes which are known in principle from the corresponding pyrocatechol monoethers of the formula (IV) and chlorosulfonyl isocyanate (cf. G. Lohaus, Chem. Ber. 105, 2791 (1972)).

The starting substances of the formula (III) are known or can be prepared by processes which are known in principle, for example by cyclizing corresponding guanidine derivatives with appropriately substituted 1,3-diketones, cf., for example, "The Chemistry of Heterocyclic Compounds", Vol. XVI (1962) and Supplement I (1970), or by derivatization of cyanuric chloride, cf., for example, "The Chemistry of Heterocyclic Compounds", L. Rapaport: "s-Triazines and Derivatives" (1959).

The reaction of the compounds (IV) with the chlorosulfonylureas (V) is preferably carried out in inert solvents, such as, for example, dichloromethane, at temperatures between −10° C. and 80° C. in the presence of a base as the HCl-binding agent. Bases which can be employed are alkali metal carbonates, alkali metal bicarbonates, alkaline earth metal carbonates or alkaline earth metal bicarbonates, such as, for example, $K_2CO_3$, $NaHCO_3$, $Na_2CO_3$, or tertiary amines, such as, for example, pyridine or triethylamine.

The pyrocatechol monothers (IV) are known from the literature or can be prepared by processes which are known from the literature. The chlorosulfonylureas (V) are accessible from the amines of the formula (III) and chlorosulfonyl isocyanate (EP-A 141,199).

The reaction of the compounds (VI) with the heterocyclic carbamates of the formula VII is preferably carried out in the presence of tertiary organic bases, such as, for example, 1,8-diazabicyclo[5.4.0]undec-7-ene (DBU), in inert solvents, such as acetonitrile or dioxane, at temperatures between 20° C. and the boiling point of the solvent (analogously to EP-A 44,807).

The carbamates (VII), which are required for this process, are known from the literature or are prepared by known processes (EP-A 70,804). The sulfamates (VI) are prepared from the pyrocatechol monoethers on which they are based by known processes (cf., for example, Synthesis 1978, 357; Z. Chem. 15, 270 (1975); Chem. Ber. 105, 2791 (1972)).

The salts of the compounds of the formula I are preferably prepared in inert solvents, such as, for example, water, methanol or acetone, at temperatures from 0°-100° C. Examples of bases which are suitable for the preparation of the salts according to the invention are alkali metal carbonates, such as potassium carbonate, alkali metal hydroxides and alkaline earth metal hydroxides, ammonia or ethanolamine.

The compounds of the formula I according to the invention have an excellent herbicidal activity against a broad range of economically important monocotyledon and dicotyledon noxious plants. The active substances act equally well on perennial weeds which produce shoots from rhizomes, rootstocks or other perennial organs and which cannot be easily controlled. In this context, it does not matter if the substances are applied before sowing, as a pre-emergence treatment or post-emergence treatment. Some representatives of the monocotyledon and dicotyledon weed flora which can be controlled may be mentioned individually as examples, but this is not to be taken to mean a restriction to certain species.

The monocotyledon weed species controlled include, for example, Avena, Lolium, Alopecurus, Phalaris, Echinochloa, Digitaria, Setaria etc. and Cyperus species from the annual group, and the perennial species include Agropyron, Cynodon, Imperata and Sorghum etc., and also perennial Cyperus species.

Of the dicotyledon weed species, the range of action covers species such as, for example, Galium, Viola, Veronica, Lamium, Stellaria, Amaranthus, Sinapis, Ipomoea, Matricaria, Abutilon, Sida etc. from the annual plants, and Convolvulus, Cirsium, Rumex, Artemisia etc. from the perennials.

Excellent control of weeds occurring under the specific culture conditions in rice, such as, for example, Sagittaria, Alisma, Eleocharis, Scirpus, Cyperus etc., by the active substances according to the invention is also possible.

If the compounds according to the invention are applied to the soil surface before germination, either emergence of the weed seedlings is prevented completely, or the weeds grow until they have reached the cotyledon stage but growth then comes to a standstill and, after a period of three to four weeks, the plants eventually die completely. When, in the post-emergence method, the active substances are applied to the green parts of the plants, growth also stops dramatically very soon after the treatment, and the weed plants remain in the growth stage of the time of application, or, after a certain period of time, die more or less rapidly, so that competition by the weeds, which is detrimental for the crop plants, can thus be prevented at a very early stage and in a sustained manner by using the novel agents according to the invention.

Even though the compounds according to the invention have an excellent herbicidal activity against monocotyledon and dicotyledon weeds, crop plants of economically important crops such as, for example, wheat, barley, rye, rice, maize, sugar beet, cotton and soya beans, are damaged only to a negligible extent, or not at all. Thus, the present compounds are very suitable for selectively controlling undesired plant growth in agricultural plantations of useful plants.

In addition, the compounds according to the invention have plant growth-regulating properties in crop plants. They have a regulating effect on the plant metabolism and can thus be employed for facilitating harvesting, such as, for example, by provoking desiccation, abscission and stunted growth. Furthermore, they are suitable for generally regulating and inhibiting undesired vegetative growth, without simultaneously destroying the plants. Inhibition of vegetative growth plays an important role in many monocotyledon and dicotyledon crops because lodging can be reduced hereby, or prevented completely.

The agents according to the invention can be employed in the conventional preparations as wettable powders, emulsifiable concentrates, emulsions, sprayable solutions, dusting agents, seed-dressing agents, dispersions, granules or microgranules.

Wettable powders are preparations which are uniformly dispersible in water and which, besides the active substance, also contain wetting agents, for example, polyoxyethylated alkylphenols, polyoxyethylated fatty alcohols, alkylsulfonates or alkylphenylsulfonates, and dispersing agents, for example, sodium ligninsulfonate, sodium 2,2'-dinaphthylmethane-6,6'-disulfonate, sodium dibutylnaphthalenesulfonate and also sodium oleoylmethyltaurinate, as well as, if appropriate, a diluent or inert substance. The formulations are prepared in a customary manner, for example by grinding and mixing of the components.

Emulsifiable concentrates can be prepared, for example, by dissolving the active substances in an inert organic solvent, for example butanol, cyclohexanone, dimethylformamide, xylene and also higher-boiling aromatics or hydrocarbons, with the addition of one or more emulsifiers. In the case of liquid active substances, all or part of the solvent component can be omitted. Emulsifiers which can be used are, for example: calcium salts of alkylarylsulfonic acid, such as Ca dodecylbenzenesulfonate, or nonionic emulsifiers, such as fatty acid polyglycol esters, alkylaryl polyglycol ethers, fatty alcohol polyglycol ethers, propylene oxide/ethylene oxide condensation products, fatty alcohol/propylene oxide/-ethylene oxide condensation products, alkyl polyglycol ethers, sorbitan fatty acid esters, polyoxyethylene sorbitan fatty acid esters or polyoxyethylene sorbitol esters.

Dusting agents are obtained by grinding the active substance with finely divided solid substances, for example talc or natural clays, such as kaolin, bentonite, pyrophillite, or diatomaceous earth.

Granules can be produced either by spraying the active substance onto adsorptive, granulated inert material or by applying active substance concentrates onto the surface of carriers such as sand, kaolinites or granulated inert material, by means of binders, for example polyvinyl alcohol, sodium polyacrylate or alternatively mineral oils. Suitable active substances can also be granulated in the manner which is conventional for the preparation of fertilizer granules, if desired in a mixture with fertilizers.

The active substance concentration in wettable powders is, for example, about 10 to 90% by weight; the remainder to 100% by weight comprises conventional formulation components. In the case of emulsifiable concentrates, the active substance concentration can be about 5 to 80% by weight. Formulations in the form of dusts usually contain 5 to 20% by weight, sprayable solutions about 2 to 20% by weight. In the case of granules, the active substance content depends partly on whether the active compound is liquid or solid and on which granulation auxiliaries, fillers etc. are used.

In addition, the active substance formulations mentioned contain, if appropriate, the adhesives, wetting agents, dispersing agents, emulsifiers, penetrants, solvents, fillers or carriers which are conventional in each case.

For use, the concentrates, present in commercially available form, are diluted, if appropriate, in a conventional manner, for example using water in the case of wettable powders, emulsifiable concentrates, dispersions and, in some cases, also in the case of microgranules. Preparations in the form of dusts and in the form of granules and also sprayable solutions are usually not further diluted with other inert substances before use.

The application rate required varies with the external conditions, such as temperature, humidity amongst others. It can vary within wide limits, for example between 0.005 and 10.0 kg/ha or more of active substance, preferably, however, it is between 0.01 and 5 kg/ha.

If appropriate, mixtures or mixed formulations with other active substances, such as, for example, insecticides, acaricides, herbicides, fertilizers, growth regulators or fungicides are also possible.

The following examples illustrate the invention in greater detail.

FORMULATION EXAMPLES

A. A dusting agent is obtained by mixing 10 parts by weight of active substance and 90 parts by weight of talc or inert substance, and comminuting the mixture in a hammer mill.

B. A wettable powder which is readily dispersible in water is obtained by mixing 25 parts by weight of active substance, 64 parts by weight of kaolin-containing quartz as inert substance, 10 parts by weight of potassium ligninsulfonate and 1 part by weight of sodium oleoylmethyltaurinate as wetting and dispersing agent, and grinding the mixture in a pinned disk mill.

C. A dispersion concentrate which is readily dispersible in water is obtained by mixing 20 parts by weight of active substance with 6 parts by weight of alkylphenol polyglycol ether (®Triton X 207), 3 parts by weight of isotridecanol polyglycol ether (8 EO) and 71 parts by weight of paraffinic mineral oil (boiling range, for example, about 255° to above 377° C.), and grinding the mixture in a ball mill to a fineness of below 5 microns.

D. An emulsifiable concentrate is obtained from 15 parts by weight of active substance, 75 parts by weight of cyclohexanone as solvent and 10 parts by weight of oxyethylated nonylphenol (10 EO) as emulsifier.

CHEMICAL EXAMPLES

Example 1

2-(2-Chloroethoxy)phenoxysulfonyl isocyanate 3.4 g (0.024 mol) of chlorosulfonyl isocyanate are added dropwise at 25° C. to a solution of 3.45 g (0.02 mol) of 2-(2-chloroethoxy)phenol in 20 ml of xylene. When the dropwise addition is complete, the temperature is increased slowly to 140° C., and the mixture is refluxed for 2 hours. The mixture is cooled and the solvent as well as excess chlorosulfonyl isocyanate are removed on a rotary evaporator. The yellow oil which remains (5.6 g = 100% of theory) is employed without further purification.

Example 2

1-[2-(2-Chloroethoxy)phenoxysulfonyl]-3-(4,6-dimethoxypyrimidin-2-yl)urea

A solution of 5.6 g (0.02 mol) of the product of Example 1 in 20 ml of dichloromethane is added dropwise at 0° C. to 3.1 g (0.02 mol) of 2-amino-4,6-dimethoxypyrimidine in 30 ml of dichloromethane. The reaction mixture is allowed to reach room temperature, and stirring is continued for 24 hours. The reaction solution is diluted using 100 ml of dichloromethane and washed with 50 ml of 1N hydrochloric acid and 50 ml of water. The organic phase is dried using sodium sulfate, and the solvent is removed on a rotary evaporator. The viscous oil which remains is crystallized by trituration with diethyl ether. 7.7 g (89% of theory) of 1-[2-(2-chloroethoxy)phenoxy-sulfonyl]-3-(4,6-dimethoxypyrimidin-2-yl)urea of melting point 132°–134° C. are obtained.

Example 3

3-(4,6-Dimethoxypyrimidin-2-yl)-1-(2-propargyloxyphenoxysulfonyl)urea 3.1 g (0.02 mol) of 2-amino-4,6-dimethoxypyrimidine are dissolved in 30 ml of dichloromethane, and 5.1 g (0.02 mol) of 2-propargyloxyphenoxysulfonyl isocyanate—dissolved in 20 ml of dichloromethane—are added at 0° C. After the reaction mixture has been stirred for 24 hours at room temperature, it is diluted with 50 ml of dichloromethane, washed with 50 ml of 1N hydrochloric acid and 50 ml of water, dried and evaporated. The oily residue crystallizes on trituration with diethyl ether. 7.4 g (91% of theory) of 3-(4,6-dimethoxypyrimidin-2-yl)-1-(2-propargyloxyphenoxysulfonyl)urea of melting point 125°–126° C. are obtained.

Example 4

3-(4,6-Dimethoxypyrimidin-2-yl)-1-[2-(2-methoxyethoxy)phenoxysulfonyl]urea 1.74 g (0.0063 mol) of phenyl N-(4,6-dimethoxypyrimidin-2-yl)carbamate are dissolved in 80 ml of acetonitrile, and 1.48 g (0.006 mol) of 2-(2-methoxyethoxy)phenyl sulfamate are added at room temperature. 1.0 g (0.0066 mol) of 1,8-diazabicyclo[5.4.0]undec-7-ene (DBU) are added and the reaction mixture is then stirred at room temperature for 18 hours, concentrated, diluted with H$_2$O and acidified with 2N hydrochloric acid to give a pH of 3–4. After the solids have been filtered off with suction and dried, 2.4 g (93% of theory) of 3-(4,6-dimethoxypyrimidin-2-yl)-1-[2-(2-methoxyethoxy)phenoxysulfonyl]urea of melting point 106°–108° C. are obtained.

The compounds of the Tables which follow are prepared in an analogous manner as described in Examples 1–4.

TABLE 1

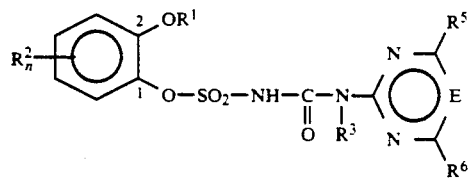

| Ex. No. | $R^1$ | $(R^2)_n$ | $R^3$ | $R^5$ | $R^6$ | E | n | m.p. [°C.] |
|---|---|---|---|---|---|---|---|---|
| 5 | $CH_2CH_2Cl$ | | H | $CH_3$ | $CH_3$ | CH | 0 | |
| 6 | " | | H | $OCH_3$ | $CH_3$ | CH | 0 | |
| 7 | " | | H | $CH_3$ | $CH_3$ | N | 0 | |
| 8 | " | | H | $OCH_3$ | $CH_3$ | N | 0 | |
| 9 | " | | H | $OCH_3$ | $OCH_3$ | N | 0 | |
| 10 | " | | H | $OCH_3$ | Cl | CH | 0 | |
| 11 | " | | H | $OCF_2H$ | $CH_3$ | CH | 0 | |
| 12 | " | | H | $OCF_2H$ | $OCF_2H$ | CH | 0 | |
| 13 | " | | H | $OCH_3$ | Br | CH | 0 | |
| 14 | " | | H | $CH_3$ | Cl | CH | 0 | |
| 15 | " | | H | $OCH_3$ | H | CH | 0 | |
| 16 | " | | H | $OCH_3$ | $NHCH_3$ | CH | 0 | |
| 17 | " | | H | $OCH_3$ | $NHCH_3$ | N | 0 | |
| 18 | " | | H | $CH_3$ | $NHCH_3$ | CH | 0 | |
| 19 | " | | H | $CH_3$ | $NHCH_3$ | N | 0 | |
| 20 | " | | H | $OCH_3$ | $SCH_3$ | CH | 0 | |
| 21 | " | | H | $OCH_3$ | $OC_2H_5$ | CH | 0 | |
| 22 | " | | H | $OCH_3$ | $OC_3H_7$ | CH | 0 | |
| 23 | " | | H | $OCH_3$ | $OC_2H_5$ | N | 0 | |
| 24 | " | | H | Cl | $OC_2H_5$ | CH | 0 | |
| 25 | " | | H | $OC_2H_5$ | $OC_2H_5$ | CH | 0 | |
| 26 | " | | H | $C_2H_5$ | $OCH_3$ | CH | 0 | |
| 27 | " | | H | $CF_3$ | $OCH_3$ | CH | 0 | |
| 28 | " | | H | $OCH_2CF_3$ | $CH_3$ | CH | 0 | |
| 29 | " | | H | $OCH_2CF_3$ | $OCH_3$ | CH | 0 | |
| 30 | " | | H | $OCH_2CF_3$ | $OCH_2CF_3$ | CH | 0 | |
| 31 | " | | H | $OCH_2CF_3$ | $NHCH_3$ | CH | 0 | |
| 32 | " | | H | $OCH_2CF_3$ | $OCH_3$ | N | 0 | |
| 33 | " | | H | $OCH_2CF_3$ | $NHCH_3$ | N | 0 | |
| 34 | " | | H | $OCH_3$ | $NHC_2H_5$ | CH | 0 | |
| 35 | " | | H | $OCH_2CF_3$ | $NHC_2H_5$ | CH | 0 | |
| 36 | " | | H | $OCH_3$ | $N(CH_3)_2$ | CH | 0 | |
| 37 | " | | H | $OCH_3$ | $CH(OCH_3)_2$ | CH | 0 | |
| 38 | $CH_2CH_2OCH_3$ | | H | $CH_3$ | $CH_3$ | CH | 0 | 103–105 |
| 39 | " | | H | $OCH_3$ | $CH_3$ | CH | 0 | |
| 40 | " | | H | $CH_3$ | $CH_3$ | N | 0 | |
| 41 | " | | H | $OCH_3$ | $CH_3$ | N | 0 | |
| 42 | " | | H | $OCH_3$ | $OCH_3$ | N | 0 | |
| 43 | " | | H | $OCH_3$ | Cl | CH | 0 | Resin |
| 44 | " | | H | $OCF_2H$ | $CH_3$ | CH | 0 | |
| 45 | " | | H | $OCF_2H$ | $OCF_2H$ | CH | 0 | |
| 46 | " | | H | $OCH_3$ | Br | CH | 0 | |
| 47 | " | | H | $CH_3$ | Cl | CH | 0 | |
| 48 | " | | H | $OCH_3$ | H | CH | 0 | |
| 49 | " | | H | $OCH_3$ | $NHCH_3$ | CH | 0 | |
| 50 | " | | H | $OCH_3$ | $NHCH_3$ | N | 0 | |
| 51 | " | | H | $CH_3$ | $NHCH_3$ | CH | 0 | |
| 52 | " | | H | $CH_3$ | $NHCH_3$ | N | 0 | |
| 53 | " | | H | $OCH_3$ | $SCH_3$ | CH | 0 | |
| 54 | " | | H | $OCH_3$ | $OC_2H_5$ | CH | 0 | |
| 55 | " | | H | $OCH_3$ | $OC_3H_7$ | CH | 0 | |
| 56 | " | | H | $OCH_3$ | $OC_2H_5$ | N | 0 | |
| 57 | " | | H | Cl | $OC_2H_5$ | CH | 0 | |
| 58 | " | | H | $OC_2H_5$ | $OC_2H_5$ | CH | 0 | |
| 59 | " | | H | $C_2H_5$ | $OCH_3$ | CH | 0 | |
| 60 | " | | H | $CF_3$ | $OCH_3$ | CH | 0 | |
| 61 | " | | H | $OCH_2CF_3$ | $CH_3$ | CH | 0 | |
| 62 | " | | H | $OCH_2CF_3$ | $OCH_3$ | CH | 0 | |
| 63 | " | | H | $OCH_2CF_3$ | $OCH_2CF_3$ | CH | 0 | |
| 64 | $CH_2CH_2OCH_3$ | | H | $OCH_2CF_3$ | $NHCH_3$ | CH | 0 | |
| 65 | " | | H | $OCH_2CF_3$ | $OCH_3$ | N | 0 | |
| 66 | " | | H | $OCH_2CF_3$ | $NHCH_3$ | N | 0 | |
| 67 | " | | H | $OCH_3$ | $OCH_3$ | CH | 0 | |
| 68 | " | | H | $OCH_2CF_3$ | $NHC_2H_5$ | CH | 0 | |
| 69 | " | | H | $OCH_3$ | $N(CH_3)_2$ | CH | 0 | |
| 70 | " | | H | $OCH_3$ | $CH(OCH_3)_2$ | CH | 0 | |
| 71 | $CH_2CH=CH_2$ | | H | $CH_3$ | $CH_3$ | CH | 0 | 128–133 |
| 72 | " | | H | $OCH_3$ | $CH_3$ | CH | 0 | 89–90 |
| 73 | " | | H | $CH_3$ | $CH_3$ | N | 0 | |
| 74 | " | | H | $OCH_3$ | $CH_3$ | N | 0 | 112–115 |
| 75 | " | | H | $OCH_3$ | $OCH_3$ | N | 0 | |

TABLE 1-continued

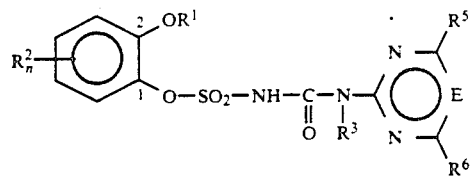

| Ex. No. | R¹ | (R²)ₙ | R³ | R⁵ | R⁶ | E | n | m.p. [°C.] |
|---|---|---|---|---|---|---|---|---|
| 76 | " | | H | OCH₃ | Cl | CH | 0 | |
| 77 | " | | H | OCF₂H | CH₃ | CH | 0 | |
| 78 | " | | H | OCF₂H | OCF₂H | CH | 0 | |
| 79 | " | | H | OCH₃ | Br | CH | 0 | |
| 80 | " | | H | CH₃ | Cl | CH | 0 | |
| 81 | " | | H | OCH₃ | H | CH | 0 | |
| 82 | " | | H | OCH₃ | NHCH₃ | CH | 0 | |
| 83 | " | | H | OCH₃ | NHCH₃ | N | 0 | |
| 84 | " | | H | OCH₃ | OCH₃ | CH | 0 | 123 |
| 85 | " | | H | CH₃ | NHCH₃ | N | 0 | |
| 86 | " | | H | OCH₃ | SCH₃ | CH | 0 | |
| 87 | " | | H | OCH₃ | OC₂H₅ | CH | 0 | |
| 88 | " | | H | OCH₃ | OC₃H₇ | CH | 0 | |
| 89 | " | | H | OCH₃ | OC₂H₅ | N | 0 | |
| 90 | " | | H | Cl | OC₂H₅ | CH | 0 | |
| 91 | " | | H | OC₂H₅ | OC₂H₅ | CH | 0 | |
| 92 | " | | H | C₂H₅ | OCH₃ | CH | 0 | |
| 93 | " | | H | CF₃ | OCH₃ | CH | 0 | |
| 94 | " | | H | OCH₂CF₃ | CH₃ | CH | 0 | |
| 95 | " | | H | OCH₂CF₃ | OCH₃ | CH | 0 | |
| 96 | CH₂CH=CH₂ | | H | OCH₂CF₃ | OCH₂CF₃ | CH | 0 | |
| 97 | " | | H | OCH₂CF₃ | NHCH₃ | CH | 0 | |
| 98 | " | | H | OCH₂CF₃ | OCH₃ | N | 0 | |
| 99 | " | | H | OCH₂CF₃ | NHCH₃ | N | 0 | |
| 100 | " | | H | OCH₃ | NHC₂H₅ | CH | 0 | |
| 101 | " | | H | OCH₂CF₃ | NHC₂H₅ | CH | 0 | |
| 102 | " | | H | OCH₃ | N(CH₃)₂ | CH | 0 | |
| 103 | " | | H | OCH₃ | CH(OCH₃)₂ | CH | 0 | |
| 104 | " | | H | OCH₃ | Cl | N | 0 | |
| 105 | CH₂C≡CH | | H | CH₃ | CH₃ | CH | 0 | 128-133 (decomp.) |
| 106 | " | | H | OCH₃ | CH₃ | CH | 0 | 143-146 |
| 107 | " | | H | CH₃ | CH₃ | N | 0 | |
| 108 | " | | H | OCH₃ | CH₃ | N | 0 | |
| 109 | " | | H | OCH₃ | OCH₃ | N | 0 | |
| 110 | " | | H | OCH₃ | Cl | CH | 0 | |
| 111 | " | | H | OCF₂H | CH₃ | CH | 0 | |
| 112 | " | | H | OCF₂H | OCF₂H | CH | 0 | |
| 113 | " | | H | OCH₃ | Br | CH | 0 | |
| 114 | " | | H | CH₃ | Cl | CH | 0 | |
| 115 | " | | H | OCH₃ | H | CH | 0 | |
| 116 | " | | H | OCH₃ | NHCH₃ | CH | 0 | |
| 117 | " | | H | OCH₃ | NHCH₃ | N | 0 | |
| 118 | " | | H | CH₃ | NHCH₃ | CH | 0 | |
| 119 | " | | H | CH₃ | NHCH₃ | N | 0 | |
| 120 | " | | H | OCH₃ | SCH₃ | CH | 0 | |
| 121 | " | | H | OCH₃ | OC₂H₅ | CH | 0 | |
| 122 | " | | H | OCH₃ | OC₃H₇ | CH | 0 | |
| 123 | " | | H | OCH₃ | OC₂H₅ | N | 0 | |
| 124 | " | | H | Cl | OC₂H₅ | CH | 0 | |
| 125 | " | | H | OC₂H₅ | OC₂H₅ | CH | 0 | |
| 126 | " | | H | C₂H₅ | OCH₃ | CH | 0 | |
| 127 | CH₂C≡CH | | H | CF₃ | OCH₃ | CH | 0 | |
| 128 | " | | H | OCH₂CF₃ | CH₃ | CH | 0 | |
| 129 | " | | H | OCH₂CF₃ | OCH₃ | CH | 0 | |
| 130 | " | | H | OCH₂CF₃ | OCH₂CF₃ | CH | 0 | |
| 131 | " | | H | OCH₂CF₃ | NHCH₃ | CH | 0 | |
| 132 | " | | H | OCH₂CF₃ | OCH₃ | N | 0 | |
| 133 | " | | H | OCH₂CF₃ | NHCH₃ | N | 0 | |
| 134 | " | | H | OCH₃ | NHC₂H₅ | CH | 0 | |
| 135 | " | | H | OCH₂CF₃ | NHC₂H₅ | CH | 0 | |
| 136 | " | | H | OCH₃ | N(CH₃)₂ | CH | 0 | |
| 137 | " | | H | OCH₃ | CH(OCH₃)₂ | CH | 0 | |
| 138 | CH₂CCl=CH₂ | | H | OCH₃ | OCH₃ | CH | 0 | |
| 139 | " | | H | OCH₃ | CH₃ | CH | 0 | |
| 140 | " | | H | OCH₃ | CH₃ | N | 0 | |
| 141 | " | | H | OCH₃ | OCH₃ | N | 0 | |
| 142 | " | | H | OCH₃ | Cl | CH | 0 | |
| 143 | " | | H | OCF₂H | CH₃ | CH | 0 | |
| 144 | " | | H | OCF₂H | OCF₂H | CH | 0 | |
| 145 | " | | H | OCH₃ | NHCH₃ | CH | 0 | |

TABLE 1-continued

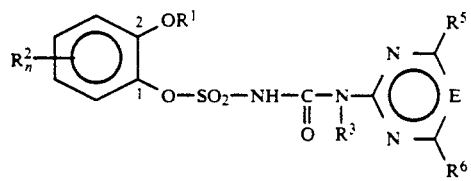

| Ex. No. | R¹ | (R²)ₙ | R³ | R⁵ | R⁶ | E | n | m.p. [°C.] |
|---|---|---|---|---|---|---|---|---|
| 146 | " | | H | Cl | $OC_2H_5$ | CH | 0 | |
| 147 | " | | H | $OCH_2CF_3$ | $OCH_3$ | CH | 0 | |
| 148 | " | | H | $OCH_2CF_3$ | $OCH_3$ | N | 0 | |
| 149 | $CH_2CH=CHCl$ | | H | $OCH_3$ | $OCH_3$ | CH | 0 | |
| 150 | " | | H | $OCH_3$ | $CH_3$ | CH | 0 | |
| 151 | " | | H | $OCH_3$ | $CH_3$ | N | 0 | |
| 152 | " | | H | $OCH_3$ | $OCH_3$ | N | 0 | |
| 153 | " | | H | $OCH_3$ | Cl | CH | 0 | |
| 154 | " | | H | $OCF_2H$ | $CH_3$ | CH | 0 | |
| 155 | " | | H | $OCF_2H$ | $OCF_2H$ | CH | 0 | |
| 156 | " | | H | $OCH_3$ | $NHCH_3$ | CH | 0 | |
| 157 | " | | H | Cl | $OC_2H_5$ | CH | 0 | |
| 158 | " | | H | $OCH_2CF_3$ | $OCH_3$ | CH | 0 | |
| 159 | $CH_2CH=Cl$ | | H | $OCH_2CF_3$ | $OCH_3$ | N | 0 | |
| 160 | $CH_2C(CH_3)=CH_2$ | | H | $OCH_3$ | $OCH_3$ | CH | 0 | |
| 161 | " | | H | $OCH_3$ | $CH_3$ | CH | 0 | |
| 162 | " | | H | $OCH_3$ | $CH_3$ | N | 0 | |
| 163 | " | | H | $OCH_3$ | $OCH_3$ | N | 0 | |
| 164 | " | | H | $OCH_3$ | Cl | CH | 0 | |
| 165 | " | | H | $OCF_2H$ | $CH_3$ | CH | 0 | |
| 166 | " | | H | $OCF_2H$ | $CF_2H$ | CH | 0 | |
| 167 | " | | H | $OCH_3$ | $NHCH_3$ | CH | 0 | |
| 168 | " | | H | Cl | $OC_2H_5$ | CH | 0 | |
| 169 | " | | H | $OCH_2CF_3$ | $OCH_3$ | CH | 0 | |
| 170 | " | | H | $OCH_2CF_3$ | $OCH_3$ | N | 0 | |
| 171 | $CH_2CH=CHCH_3$ | | H | $OCH_3$ | $OCH_3$ | CH | 0 | |
| 172 | " | | H | $OCH_3$ | $CH_3$ | CH | 0 | |
| 173 | " | | H | $OCH_3$ | $CH_3$ | N | 0 | |
| 174 | " | | H | $OCH_3$ | $OCH_3$ | N | 0 | |
| 175 | " | | H | $OCH_3$ | Cl | CH | 0 | |
| 176 | " | | H | $OCF_2H$ | $CH_3$ | CH | 0 | |
| 177 | " | | H | $OCF_2H$ | $OCF_2H$ | CH | 0 | |
| 178 | " | | H | $OCH_3$ | $NHCH_3$ | CH | 0 | |
| 179 | " | | H | Cl | $OC_2H_5$ | CH | 0 | |
| 180 | " | | H | $OCH_2CF_3$ | $OCH_3$ | CH | 0 | |
| 181 | " | | H | $OCH_2CF_3$ | $OCH_3$ | N | 0 | |
| 182 | $CH_2C \equiv CCH_3$ | | H | $OCH_3$ | $OCH_3$ | CH | 0 | |
| 183 | " | | H | $OCH_3$ | $CH_3$ | CH | 0 | |
| 184 | " | | H | $OCH_3$ | $CH_3$ | N | 0 | |
| 185 | " | | H | $OCH_3$ | $OCH_3$ | N | 0 | |
| 186 | " | | H | $OCH_3$ | Cl | CH | 0 | |
| 187 | " | | H | $OCF_2H$ | $CH_3$ | CH | 0 | |
| 188 | " | | H | $OCF_2H$ | $OCF_2H$ | CH | 0 | |
| 189 | " | | H | $OCH_3$ | $NHCH_3$ | CH | 0 | |
| 190 | " | | H | Cl | $OC_2H_5$ | CH | 0 | |
| 191 | " | | H | $OCH_2CF_3$ | $OCH_3$ | CH | 0 | |
| 192 | $CH_2C \equiv CCH_3$ | | H | $OCH_2CF_3$ | $OCH_3$ | N | 0 | |
| 193 | $CH_2CH_2Br$ | | H | $OCH_3$ | $OCH_3$ | CH | 0 | |
| 194 | " | | H | $OCH_3$ | $CH_3$ | CH | 0 | |
| 195 | " | | H | $OCH_3$ | $CH_3$ | N | 0 | |
| 196 | " | | H | $OCH_3$ | $OCH_3$ | N | 0 | |
| 197 | " | | H | $OCH_3$ | Cl | CH | 0 | |
| 198 | " | | H | $OCF_2H$ | $CH_3$ | CH | 0 | |
| 199 | " | | H | $OCF_2H$ | $OCF_2H$ | CH | 0 | |
| 100 | " | | H | $OCH_3$ | $NHCH_3$ | CH | 0 | |
| 101 | " | | H | Cl | $OC_2H_5$ | CH | 0 | |
| 102 | " | | H | $OCH_2CF_3$ | $OCH_3$ | CH | 0 | |
| 203 | " | | H | $OCH_2CF_3$ | $OCH_3$ | N | 0 | |
| 204 | $CH_2CH(OCH_3)_2$ | | H | $OCH_3$ | $OCH_3$ | CH | 0 | |
| 205 | " | | H | $OCH_3$ | $CH_3$ | CH | 0 | |
| 206 | " | | H | $OCH_3$ | $CH_3$ | N | 0 | |
| 207 | $C_6H_5$ | | H | $OCH_3$ | $OCH_3$ | CH | 0 | 117–119 |
| 208 | " | | H | $OCH_3$ | $CH_3$ | CH | 0 | 138–139 |
| 209 | " | | H | $OCH_3$ | $CH_3$ | N | 0 | 120–122 |
| 210 | " | | H | $CH_3$ | Cl | CH | 0 | 147–148 |
| 211 | " | | H | $OCH_3$ | Cl | CH | 0 | |
| 212 | " | | H | $CH_3$ | $CH_3$ | CH | 0 | 136–138 |
| 213 | $CF_2CHFCF_3$ | | H | $OCH_3$ | $OCH_3$ | CH | 0 | 122–124 |
| 214 | " | | H | $OCH_3$ | $CH_3$ | CH | 0 | |
| 215 | " | | H | Cl | $OCH_3$ | CH | 0 | 160–162 |
| 216 | " | | H | $OCH_3$ | $CH_3$ | N | 0 | |

TABLE 1-continued

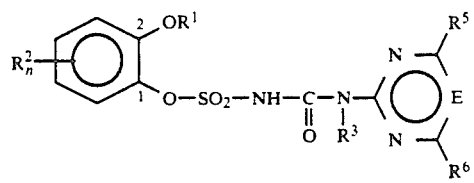

| Ex. No. | R¹ | (R²)ₙ | R³ | R⁵ | R⁶ | E | n | m.p. [°C.] |
|---|---|---|---|---|---|---|---|---|
| 217 | " | | H | OCH$_3$ | CH$_3$ | CH$_3$ | 0 | Resin |
| 218 | CH$_2$C$_6$H$_5$ | | H | OCH$_3$ | OCH$_3$ | CH | 0 | |
| 219 | " | | H | OCH$_3$ | CH$_3$ | CH | 0 | |
| 220 | CF$_2$CClFH | | H | OCH$_3$ | Cl | CH | 0 | 106-110 |
| 221 | CCH$_3$CH=CH$_2$ | | H | OCH$_3$ | OCH$_3$ | CH | 0 | |
| 222 | " | | H | OCH$_3$ | CH$_3$ | CH | 0 | |
| 223 | " | | H | OCH$_3$ | CH$_3$ | N | 0 | |
| 224 | C$_5$H$_9$ | | H | OCH$_3$ | OCH$_3$ | CH | 0 | |
| 225 | C$_5$H$_9$ | | H | OCH$_3$ | CH$_3$ | CH | 0 | |
| 226 | CF$_2$CClFH | | H | CH$_3$ | CH$_3$ | CH | 0 | 63-66 |
| 227 | " | | H | OCH$_3$ | OCH$_3$ | CH | 0 | 109-110 |
| 228 | " | | H | OCH$_3$ | CH$_3$ | CH | 0 | |
| 229 | " | | H | OCH$_3$ | CH$_3$ | N | 0 | |
| 230 | CH$_2$CH=CH$_2$ | 6-CH$_3$ | H | OCH$_3$ | OCH$_3$ | CH | | |
| 231 | " | 6-CH$_3$ | H | OCH$_3$ | CH$_3$ | CH | | |
| 232 | " | 6-CH$_3$ | H | OCH$_3$ | CH$_3$ | N | | |
| 233 | CH$_2$CH$_2$Cl | 6-CH$_3$ | H | OCH$_3$ | OCH$_3$ | CH | | |
| 234 | " | 6-CH$_3$ | H | OCH$_3$ | CH$_3$ | CH | | |
| 235 | " | 6-CH$_3$ | H | OCH$_3$ | CH$_3$ | N | | |
| 236 | CH$_2$C≡CH | 6-CH$_3$ | H | OCH$_3$ | OCH$_3$ | CH | | |
| 237 | " | 6-CH$_3$ | H | OCH$_3$ | CH$_3$ | CH | | |
| 238 | " | 6-CH$_3$ | H | OCH$_3$ | CH$_3$ | N | | |
| 239 | CH$_2$CH$_2$OCH$_3$ | 6-CH$_3$ | H | OCH$_3$ | OCH$_3$ | CH | | |
| 240 | " | 6-CH$_3$ | H | OCH$_3$ | CH$_3$ | CH | | |
| 241 | " | 6-CH$_3$ | H | OCH$_3$ | CH$_3$ | N | | |
| 242 | CH$_2$C$_6$H$_5$ | 6-CH$_3$ | H | OCH$_3$ | OCH$_3$ | CH | | |
| 243 | " | 6-CH$_3$ | H | OCH$_3$ | CH$_3$ | CH | | |
| 244 | " | 6-CH$_3$ | H | OCH$_3$ | CH$_3$ | N | | |
| 245 | CCH$_3$CH=CH$_2$ | 6-CH$_3$ | H | OCH$_3$ | OCH$_3$ | CH | | |
| 246 | " | 6-CH$_3$ | H | OCH$_3$ | CH$_3$ | CH | | |
| 247 | " | 6-CH$_3$ | H | OCH$_3$ | CH$_3$ | N | | |
| 248 | C$_5$H$_9$ | 6-CH$_3$ | H | OCH$_3$ | OCH$_3$ | CH | | |
| 249 | C$_5$H$_9$ | 6-CH$_3$ | H | OCH$_3$ | CH$_3$ | CH | | |
| 250 | C$_5$H$_9$ | 6-CH$_3$ | H | OCH$_3$ | CH$_3$ | N | | |
| 251 | CH$_2$CH=CH$_2$ | 5-CH$_3$ | H | OCH$_3$ | OCH$_3$ | CH | | |
| 252 | CH$_2$CH=CH$_2$ | 5-CH$_3$ | H | OCH$_3$ | CH$_3$ | CH | | |
| 253 | CH$_2$CH$_2$Cl | 5-CH$_3$ | H | OCH$_3$ | CH$_3$ | N | | |
| 254 | " | 5-CH$_3$ | H | OCH$_3$ | OCH$_3$ | CH | | |
| 255 | CH$_2$CH$_2$OCH$_3$H | 5-CH$_3$ | H | OCH$_3$ | CH$_3$ | CH | | |
| 256 | " | 5-CH$_3$ | H | OCH$_3$ | CH$_3$ | N | | |
| 257 | CH$_2$C≡CH | 5-CH$_3$ | H | OCH$_3$ | OCH$_3$ | CH | | |
| 258 | " | 5-CH$_3$ | H | OCH$_3$ | CH$_3$ | CH | | |
| 259 | CH$_2$CH$_2$Br | 4-CH$_3$ | H | OCH$_3$ | CH$_3$ | N | | |
| 260 | " | 4-CH$_3$ | H | OCH$_3$ | OCH$_3$ | CH | | |
| 261 | CH$_2$C≡CCH$_3$ | 3-CH$_3$ | H | OCH$_3$ | CH$_3$ | CH | | |
| 262 | " | 3-CH$_3$ | H | OCH$_3$ | CH$_3$ | N | | |
| 263 | CH$_2$CH=CH$_2$ | 6-Cl | H | OCH$_3$ | OCH$_3$ | CH | | |
| 264 | " | 6-Cl | H | OCH$_3$ | CH$_3$ | CH | | |
| 265 | " | 6-Cl | H | OCH$_3$ | CH$_3$ | N | | |
| 266 | CH$_2$CH$_2$Cl | 6-Cl | H | OCH$_3$ | OCH$_3$ | CH | | |
| 267 | " | 6-Cl | H | OCH$_3$ | CH$_3$ | CH | | |
| 268 | " | 6-Cl | H | OCH$_3$ | CH$_3$ | N | | |
| 269 | CH$_2$C≡CH | 6-Cl | H | OCH$_3$ | OCH$_3$ | CH | | |
| 270 | " | 6-Cl | H | OCH$_3$ | CH$_3$ | CH | | |
| 271 | " | 6-Cl | H | OCH$_3$ | CH$_3$ | N | | |
| 272 | CH$_2$CH$_2$OCH$_3$ | 6-Cl | H | OCH$_3$ | OCH$_3$ | CH | | |
| 273 | " | 6-Cl | H | OCH$_3$ | CH$_3$ | CH | | |
| 274 | " | 6-Cl | H | OCH$_3$ | CH$_3$ | N | | |
| 275 | CH$_2$CCH$_3$=CH$_2$ | 6-Cl | H | OCH$_3$ | OCH$_3$ | CH | | |
| 276 | " | 6-Cl | H | OCH$_3$ | CH$_3$ | CH | | |
| 277 | " | 6-Cl | H | OCH$_3$ | CH$_3$ | N | | |
| 278 | C$_6$H$_5$ | 6-Cl | H | OCH$_3$ | OCH$_3$ | CH | | |
| 279 | " | 6-Cl | H | OCH$_3$ | CH$_3$ | CH | | |
| 280 | " | 6-Cl | H | OCH$_3$ | CH$_3$ | N | | |
| 281 | CH$_2$CH(OCH$_3$)$_2$ | 6-Cl | H | OCH$_3$ | OCH$_3$ | CH | | |
| 282 | " | 6-Cl | H | OCH$_3$ | CH$_3$ | CH | | |
| 283 | " | 6-Cl | H | OCH$_3$ | CH$_3$ | N | | |
| 284 | CH$_2$CH=CH$_2$ | 5-Cl | H | OCH$_3$ | OCH$_3$ | CH | | |
| 285 | " | 5-Cl | H | OCH$_3$ | CH$_3$ | CH | | |
| 286 | CH$_2$CH$_2$Cl | 4-Cl | H | OCH$_3$ | CH$_3$ | N | | |
| 287 | CH$_2$CH$_2$Cl | 5-Cl | H | OCH$_3$ | OCH$_3$ | CH | | |

TABLE 1-continued

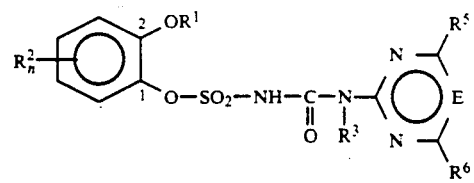

| Ex. No. | R¹ | (R²)ₙ | R³ | R⁵ | R⁶ | E | n | m.p. [°C.] |
|---|---|---|---|---|---|---|---|---|
| 288 | CH₂CH₂OCH₃ | 5-Cl | OCH₃ | OCH₃ | CH | | | |
| 289 | " | 5-Cl | H | OCH₃ | CH₃ | N | | |
| 290 | CH₂C≡CH | 5-Cl | H | OCH₃ | OCH₃ | CH | | |
| 291 | " | 5-Cl | H | OCH₃ | CH₃ | CH | | |
| 292 | CH₂CH=CHCl | 4-Cl | H | OCH₃ | CH₃ | N | | |
| 293 | " | 4-Cl | H | OCH₃ | OCH₃ | CH | | |
| 294 | CH₂C₆H₅ | 3-Cl | H | OCH₃ | OCH₃ | CH | | |
| 295 | " | 3-Cl | H | OCH₃ | CH₃ | N | | |
| 296 | CH₂CH=CH₂ | 6-F | H | OCH₃ | OCH₃ | CH | | |
| 297 | " | 6-F | H | OCH₃ | CH₃ | CH | | |
| 298 | " | 6-F | H | OCH₃ | CH₃ | N | | |
| 299 | CH₂H₂Cl | 6-F | H | OCH₃ | OCH₃ | CH | | |
| 300 | " | 6-F | H | OCH₃ | CH₃ | CH | | |
| 301 | " | 6-F | H | OCH₃ | CH₃ | N | | |
| 302 | CH₂C≡CH | 6-F | H | OCH₃ | OCH₃ | CH | | |
| 303 | " | 6-F | H | OCH₃ | CH₃ | CH | | |
| 304 | " | 6-F | H | OCH₃ | CH₃ | N | | |
| 305 | CH₂CH₂OCH₃ | 6-F | H | OCH₃ | OCH₃ | CH | | |
| 306 | " | 6-F | H | OCH₃ | CH₃ | CH | | |
| 307 | " | 6-F | H | OCH₃ | CH₃ | N | | |
| 308 | CH₂CH=CHCH₃ | 6-F | H | OCH | OCH₃ | CH | | |
| 309 | " | 6-F | H | OCH₃ | CH₃ | CH | | |
| 310 | " | 6-F | H | OCH₃ | CH₃ | N | | |
| 311 | CF₂CClFH | 6-F | H | OCH₃ | OCH₃ | CH | | |
| 312 | " | 6-F | H | OCH₃ | CH₃ | CH | | |
| 313 | " | 6-F | H | OCH₃ | CH₃ | N | | |
| 314 | CH₂C≡CCH₃ | 6-F | H | OCH | OCH | CH | | |
| 315 | " | 6-F | H | OCH₃ | CH₃ | CH | | |
| 316 | " | 6-F | H | OCH₃ | CH₃ | N | | |
| 317 | CH₂CH=CH₂ | 5-F | H | OCH₃ | OCH₃ | CH | | |
| 318 | CH₂CH=CH₂ | 5-F | H | OCH₃ | CH₃ | CH | | |
| 319 | CH₂CH₂Cl | 5-F | H | OCH₃ | CH₃ | N | | |
| 320 | " | 5-F | H | OCH₃ | OCH₃ | CH | | |
| 321 | CH₂CH₂OCH₃ | 5-F | H | OCH₃ | OCH₃ | CH | | |
| 322 | " | 5-F | H | OCH₃ | CH₃ | N | | |
| 323 | CH₂C≡CH | 5-F | H | OCH₃ | OCH₃ | CH | | |
| 324 | " | 5-F | H | OCH₃ | CH₃ | CH | | |
| 325 | CH₂CH₂Br | 4-F | H | OCH₃ | CH₃ | N | | |
| 326 | " | 4-F | H | OCH₃ | OCH₃ | CH | | |
| 327 | C₅H₉ | 3-F | H | OCH₃ | OCH₃ | CH | | |
| 328 | C₅H₉ | 3-F | H | OCH₃ | CH₃ | N | | |
| 329 | CH₂CH=CH₂ | 6-COOCH₃ | H | OCH₃ | OCH₃ | CH | | |
| 330 | " | 6-COOCH₃ | H | OCH₃ | CH₃ | CH | | |
| 331 | " | 6-COOCH₃ | H | OCH₃ | CH₃ | N | | |
| 332 | CH₂CH₂Cl | 6-COOCH₃ | H | OCH₃ | OCH₃ | CH | | |
| 333 | " | 6-COOCH₃ | H | OCH₃ | CH₃ | CH | | |
| 334 | " | 6-COOCH₃ | H | OCH₃ | CH₃ | N | | |
| 335 | CH₂C≡CH | 6-COOCH₃ | H | OCH₃ | OCH₃ | CH | | |
| 336 | " | 6-COOCH₃ | H | OCH₃ | CH₃ | CH | | |
| 337 | " | 6-COOCH₃ | H | OCH₃ | CH₃ | N | | |
| 338 | CH₂CH₂OCH₃ | 6-COOCH₃ | H | OCH₃ | OCH₃ | CH | | |
| 339 | " | 6-COOCH₃ | H | OCH₃ | CH₃ | CH | | |
| 340 | " | 6-COOCH₃ | H | OCH₃ | CH₃ | N | | |
| 341 | CH₂CH=CHCH₃ | 6-COOCH₃ | H | OCH₃ | OCH₃ | CH | | |
| 342 | " | 6-COOCH₃ | H | OCH₃ | CH₃ | CH | | |
| 343 | " | 6-COOCH₃ | H | OCH₃ | CH₃ | N | | |
| 344 | CH₂CH=CHCl | 6-COOCH₃ | H | OCH₃ | OCH₃ | CH | | |
| 345 | " | 6-COOCH₃ | H | OCH₃ | CH₃ | CH | | |
| 346 | " | 6-COOCH₃ | H | OCH₃ | CH₃ | N | | |
| 347 | C₆H₅ | 6-COOCH₃ | H | OCH₃ | OCH₃ | CH | | |
| 348 | " | 6-COOCH₃ | H | OCH₃ | CH₃ | CH | | |
| 349 | " | 6-COOCH₃ | H | OCH₃ | CH₃ | N | | |
| 350 | CH₂CH=CH₂ | 5-COOCH₃ | H | OCH₃ | OCH₃ | CH | | |
| 351 | " | 5-COOCH₃ | H | OCH₃ | CH₃ | CH | | |
| 352 | CH₂CH₂Cl | 5-COOCH₃ | H | OCH₃ | CH₃ | N | | |
| 353 | CH₂CH₂Cl | 5-COOCH₃ | H | OCH₃ | OCH₃ | CH | | |
| 354 | CH₂CH₂OCH₃ | 5-COOCH₃ | H | OCH₃ | OCH₃ | CH | | |
| 355 | " | 5-COOCH₃ | H | OCH₃ | CH₃ | N | | |
| 356 | CH₂C≡CH | 5-COOCH₃ | H | OCH₃ | OCH₃ | CH | | |
| 357 | " | 5-COOCH₃ | H | OCH₃ | CH₃ | CH | | |
| 358 | CH₂CH₂Br | 4-COOCH₃ | H | OCH₃ | CH₃ | N | | |

TABLE 1-continued

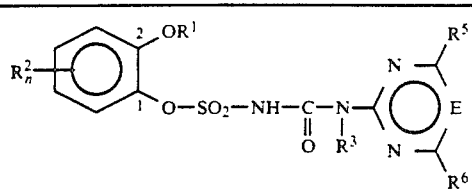

| Ex. No. | R¹ | (R²)ₙ | R³ | R⁵ | R⁶ | E | n | m.p. [°C.] |
|---|---|---|---|---|---|---|---|---|
| 359 | " | 4-COOCH₃ | H | OCH₃ | OCH₃ | CH | | |
| 360 | CH₂CCl=CH₂ | 3-COOCH₃ | H | OCH₃ | OCH₃ | CH | | |
| 361 | " | 3-COOCH₃ | H | OCH₃ | CH₃ | N | | |
| 362 | CH₂CH=CH₂ | 6-CH₂CH=CH₂ | H | OCH₃ | OCH₃ | CH | | |
| 363 | " | 6-CH₂CH=CH₂ | H | OCH₃ | CH₃ | CH | | |
| 364 | " | 6-CH₂CH=CH₂ | H | OCH₃ | CH₃ | N | | |
| 365 | CH₂CH₂Cl | 6-CH₂CH=CH₂ | H | OCH₃ | OCH₃ | CH | | |
| 366 | " | 6-CH₂CH=CH₂ | H | OCH₃ | CH₃ | CH | | |
| 367 | " | 6-CH₂CH=CH₂ | H | OCH₃ | CH₃ | N | | |
| 368 | CH₂C≡CH | 6-CH₂CH=CH₂ | H | OCH₃ | OCH₃ | CH | | |
| 369 | " | 6-CH₂CH=CH₂ | H | OCH₃ | CH₃ | CH | | |
| 370 | " | 6-CH₂CH=CH₂ | H | OCH₃ | CH₃ | N | | |
| 371 | CH₂CH₂OCH₃ | 6-CH₂CH=CH₂ | H | OCH₃ | OCH₃ | CH | | |
| 372 | " | 6-CH₂CH=CH₂ | H | OCH₃ | CH₃ | CH | | |
| 373 | " | 6-CH₂CH=CH₂ | H | OCH₃ | CH₃ | N | | |
| 374 | CH₂CH₃ | 6-CH₂CH=CH₂ | H | OCH₃ | OCH₃ | CH | | 131–132 |
| 375 | " | 6-CH₂CH=CH₂ | H | OCH₃ | CH₃ | CH | | 134–136 |
| 376 | " | 6-CH₂CH=CH₂ | H | OCH₃ | CH₃ | N | | |
| 377 | CH(CH₃)₂ | 6-CH₂CH=CH₂ | H | OCH₃ | OCH₃ | CH | | |
| 378 | " | 6-CH₂CH=CH₂ | H | OCH₃ | CH₃ | CH | | |
| 379 | " | 6-CH₂CH=CH₂ | H | OCH₃ | CH₃ | N | | |
| 380 | CH₂CH₂CH₃ | 6-CH₂CH=CH₂ | H | OCH₃ | OCH₃ | CH | | |
| 381 | " | 6-CH₂CH=CH₂ | H | OCH₃ | CH₃ | CH | | |
| 382 | " | 6-CH₂CH=CH₂ | H | OCH₃ | CH₃ | N | | |
| 383 | CH₂CH=CH₂ | 6-CH₂CH₃ | H | OCH₃ | OCH₃ | CH | | |
| 384 | " | 6-CH₂CH₃ | H | OCH₃ | CH₃ | CH | | |
| 385 | CH₂CH₂Cl | 6-CH₂CH₃ | H | OCH₃ | CH₃ | N | | |
| 386 | " | 6-CH₂CH₃ | H | OCH₃ | OCH₃ | CH | | |
| 387 | CH₂CH₂OCH₃ | 6-CH₂CH₃ | H | OCH₃ | OCH₃ | CH | | |
| 388 | CH₂CH₂OCH₃ | 6-CH₂CH₃ | H | OCH₃ | CH₃ | N | | |
| 389 | CH₂C≡CH | 6-CH₂CH₃ | H | OCH₃ | OCH₃ | CH | | |
| 390 | " | 6-CH₂CH₃ | H | OCH₃ | CH₃ | CH | | |
| 391 | CH₂CH₂Br | 6-CH₂CH₃ | H | OCH₃ | CH₃ | N | | |
| 392 | " | 6-CH₂CH₃ | H | OCH₃ | OCH₃ | CH | | |
| 393 | CH₂CCl=CH₂ | 6-CH₂CH₃ | H | OCH₃ | OCH | CH | | |
| 394 | " | 6-CH₂CH₃ | H | OCH₃ | CH₃ | N | | |
| 395 | CH₂CH=CH₂ | 6-OCH₃ | H | OCH₃ | OCH₃ | CH | | |
| 396 | " | 6-OCH₃ | H | OCH₃ | CH₃ | CH | | |
| 397 | CH₂CH₂Cl | 6-OCH₃ | H | OCH₃ | CH₃ | N | | |
| 398 | " | 6-OCH₃ | H | OCH₃ | OCH₃ | CH | | |
| 399 | CH₂CH₂OCH₃ | 6-OCH₃ | H | OCH₃ | OCH₃ | CH | | |
| 400 | " | 6-OCH₃ | H | OCH₃ | CH₃ | N | | |
| 401 | CH₂C≡CH | 6-OCH₃ | H | OCH₃ | OCH₃ | CH | | |
| 402 | " | 6-OCH₃ | H | OCH₃ | CH₃ | CH | | |
| 403 | CH₂CH₂Cl | 6-OC₆H₅ | H | OCH₃ | CH₃ | N | | |
| 404 | " | 6-OC₆H₅ | H | OCH₃ | OCH₃ | CH | | |
| 405 | CH₂CH=CH₂ | 6-OC₆H₅ | H | OCH₃ | OCH₃ | CH | | |
| 406 | " | 6-OC₆H₅ | H | OCH₃ | CH₃ | N | | |
| 407 | CH₂C≡CH | 6-OC₆H₅ | H | OCH₃ | OCH₃ | CH | | |
| 408 | " | 6-OC₆H₅ | H | OCH₃ | CHHD 3 | CH | | |
| 409 | CH₂CH₂OCH₃ | 6-OC₆H₅ | H | OCH₃ | CH₃ | N | | |
| 410 | " | 6-OC₆H₅ | H | OCH₃ | OCH₃ | CH | | |
| 411 | " | 6-C₆H₅ | H | OCH₃ | OCH₃ | CH | | |
| 412 | " | 6-C₆H₅ | H | OCH₃ | CH₃ | N | | |
| 413 | CH₂C≡CH | 6-C₆H₅ | H | OCH₃ | OCH₃ | CH | | |
| 414 | " | 6-C₆H₅ | H | OCH₃ | CH₃ | CH | | |
| 415 | CH₂CH₂Br | 6-SO₂CH₃ | H | OCH₃ | CH₃ | N | | |
| 416 | " | 6-SO₂CH₃ | H | OCH₃ | OCH₃ | CH | | |
| 417 | CH₂CCl=CH₂ | 6-SO₂CH₃ | H | OCH₃ | OCH₃ | CH | | |
| 418 | " | 6-SO₂CH₃ | H | OCH₃ | CH₃ | N | | |
| 419 | CH₂CH=CH₂ | 6-SOCH₃ | H | OCH₃ | OCH₃ | CH | | |
| 420 | " | 6-SOCH₃ | H | OCH₃ | CH₃ | CH | | |
| 421 | CH₂CH₂Cl | 6-SOCH₃ | H | OCH₃ | CH₃ | N | | |
| 422 | " | 6-SOCH₃ | H | OCH₃ | OCH₃ | CH | | |
| 423 | CH₂CH₂OCH₃ | 6-SCH₃ | H | OCH₃ | OCH₃ | CH | | |
| 424 | " | 6-SCH₃ | H | OCH₃ | CH₃ | N | | |
| 425 | CH₂C≡CH | 6-SCH₃ | H | OCH₃ | OCH₃ | CH | | |
| 426 | " | 6-SCH₃ | H | OCH₃ | CH₃ | CH | | |
| 427 | CH₂CH₂Br | 6-CF₃ | H | OCH₃ | CH₃ | N | | |
| 428 | " | 6-CF₃ | H | OCH₃ | OCH₃ | CH | | |
| 429 | CH₂CCl=CH₂ | 6-NO₂ | H | OCH₃ | OCH₃ | CH | | |

TABLE 1-continued

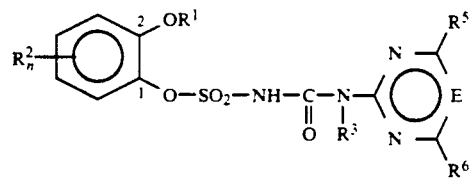

| Ex. No. | R[1] | (R[2])n | R[3] | R[5] | R[6] | E | n | m.p. [°C.] |
|---|---|---|---|---|---|---|---|---|
| 430 | CH₂CH₂Cl | 4,6-Cl₂ | H | OCH₃ | Cl | CH | | |
| 431 | " | 4,6-Cl₂ | H | OCH₃ | OCH₃ | CH | | |
| 432 | " | 4,6-Cl₂ | H | OCH₃ | CH₃ | N | | |
| 433 | " | 3,5-Cl₂ | H | OCH₃ | OCH₃ | CH | | |
| 434 | CH₂CH₂OCH₃ | 4,6-Cl₂ | H | OCH₃ | Cl | CH | | |
| 435 | " | 4,6-F₂ | H | OCH₃ | OCH₃ | CH | | |
| 436 | " | 4,6-F₂ | H | OCH₃ | CH₃ | CH | | |
| 437 | " | 3,5-F₂ | H | OCH₃ | OCH₃ | CH | | |
| 438 | CH₂CH=CH₂ | 4,6-F₂ | H | OCH₃ | CH₃ | N | | |
| 439 | " | 4,6-Cl₂ | H | OCH₃ | OCH₃ | CH | | |
| 440 | " | 4,6-Cl₂ | H | OCH₃ | Cl | CH | | |
| 441 | " | 3,5-Cl₂ | H | OCH₃ | OCH₃ | CH | | |
| 442 | CH₂C≡CH | 4,6-Cl₂ | H | OCF₂H | CH₃ | CH | | |
| 443 | " | 4,6-F₂ | H | OCH₃ | OCH₃ | CH | | |
| 444 | " | 4,6-F₂ | H | OCH₃ | CH₃ | N | | |
| 445 | " | 3,5-F₂ | H | OCH₃ | OCH₃ | CH | | |
| 446 | C₆H₅ | 4,6-F₂ | H | OCH₃ | Cl | CH | | |
| 447 | " | 4,6-Cl₂ | H | OCH₃ | OCH₃ | CH | | |
| 448 | CH₂C₆H₅ | 4,6-Cl₂ | H | OCF₂H | OCF₂H | CH | | |
| 449 | " | 4,6-F₂ | H | OCH₃ | OCH₃ | CH | | |
| 450 | CH₂CH=CHCH₃ | 4,6-F₂ | H | OCH₃ | CH₃ | N | | |
| 451 | " | 4,6-Cl₂ | H | OCH₃ | OCH₃ | CH | | |
| 452 | CH₂CH=CHCl | 4,6-Cl₂ | H | OCH₃ | Cl | CH | | |
| 453 | " | 4,6-(CH₃)₂ | H | OCH₃ | OCH₃ | CH | | |
| 454 | " | 4,6-(NO₂)₂ | H | OCH₂CF₃ | OCH₃ | CH | | |
| 455 | CH₂CH₂Cl | H | CH₃ | OCH₃ | OCH₃ | CH | | |
| 456 | " | H | CH₃ | OCH₃ | CH₃ | N | | |
| 457 | " | H | CH₂CH=CH₂ | OCH₃ | OCH₃ | CH | | |
| 458 | " | H | CH₂CH=CH₂ | OCH₃ | Cl | CH | | |
| 459 | CH₂CH₂OCH₃ | H | CH₃ | OCH₃ | OCH₃ | CH | | |
| 460 | " | H | CH₃ | OCH₃ | CH₃ | CH | | |
| 461 | " | H | CH₂CH=CH₂ | OCH₃ | | CH | | |
| 462 | " | H | CH₂CH=CH₂ | OCH₃ | CH₃ | N | | |
| 463 | CH₂CH=CH₂ | H | CH₃ | OCH₃ | OCH₃ | CH | | |
| 464 | " | H | CH₃ | OCH₃ | Cl | CH | | |
| 465 | " | H | CH₂CH=CH₂ | OCH₃ | | CH | | |
| 466 | " | H | CH₂CH=CH₂ | OCF₂H | CH₃ | CH | | |
| 467 | CH₂C≡CH | H | CH₃ | OCH₃ | OCH₃ | CH | | |
| 468 | " | H | CH₃ | OCH₃ | CH₃ | N | | |
| 469 | " | H | CH₂CH=CH₂ | OCH₃ | OCH₃ | CH | | |
| 470 | " | H | CH₂CH=CH₂ | OCH₃ | Cl | CH | | |
| 471 | CH₂C≡CCH₃ | H | CH₃ | OCH₃ | OCH₃ | CH | | |
| 472 | " | H | CH₂CH=CH₂ | OCF₂H | OCF₂H | CH | | |
| 473 | CH₂CH=CHCl | H | CH₂CH=CH₂ | OCH₃ | OCH₃ | CH | | |
| 474 | " | H | CH₃ | OCH₃ | CH₃ | N | | |
| 475 | C₆H₅ | H | C₂H₅ | OCH₃ | OCH₃ | CH | | |
| 476 | CH₂CH₂Br | H | C₂H₅ | OCH₃ | Cl | CH | | |
| 477 | CH₂CCH₃=CH₂ | H | C₂H₅ | OCH₃ | OCH₃ | CH | | |
| 478 | CH₂CF₃ | H | C₂H₅ | OCH₂CF₃ | OCH₃ | CH | | |
| 479 | CH₂C≡CH | H | C₂H₅ | OCH₃ | OCH₃ | CH | | |
| 480 | CH₂C₆H₅ | 6-CH₃ | CH₃ | OCH₃ | CH₃ | N | | |
| 481 | CH₂CH₂OCH₃ | 6-OCH₃ | CH₃ | OCH₃ | OCH₃ | CH | | |
| 482 | CH₂CH=CH₂ | 6-Cl | CH₂CH=CH₂ | OCH₃ | Cl | CH | | |
| 483 | CH₂CH(OCH₃)₂ | 6-F | CH₂CH=CH₂ | OCH₃ | OCH₃ | CH | | |
| 484 | CH₂C≡CH | 6-CF₃ | CH₃ | OCH₂CF₃ | OCH₃ | N | | |

TABLE 2

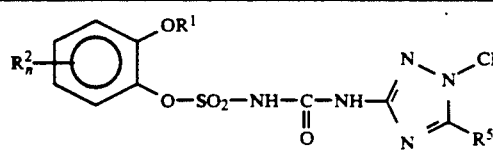

| Ex. No. | R[1] | (R[2])n | R[5] | m.p. |
|---|---|---|---|---|
| 485 | CH₂CH=CH₂ | H | CH₃ | |
| 486 | " | H | H | |
| 487 | " | H | OCH₃ | |

TABLE 2-continued

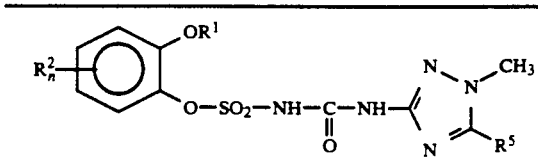

| Ex. No. | R[1] | (R[2])n | R[5] | m.p. |
|---|---|---|---|---|
| 488 | CH₂CH₂Cl | H | OCH₃ | |
| 489 | CH₂CH₂OCH₃ | H | OCH₃ | |
| 490 | CH₂C≡CH | H | OCH₃ | |

TABLE 2-continued

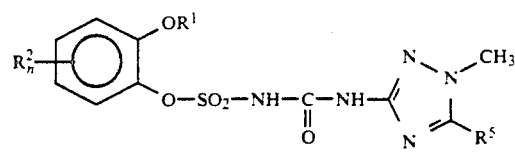

| Ex. No. | R¹ | (R²)ₙ | R⁵ | m.p. |
|---|---|---|---|---|
| 491 | CH₂C₆H₅ | H | OCH₃ | |
| 492 | CH₂CH=CHCl | H | OCH₃ | |
| 493 | CH₂CH=CHCH₃ | H | OCH₃ | |
| 494 | CH₂CH₂Br | H | OCH₃ | |
| 495 | CH₂C≡CCH₃ | H | OCH₃ | |
| 496 | C₅H₉ | H | OCH₃ | |
| 497 | CH₂CH=CH₂ | 6-CH₃ | OCH₃ | |
| 498 | CH₂CH₂Cl | 6-OCH₃ | OCH₃ | |
| 499 | CH₂CH₂OCH₃ | 6-Cl | OCH₃ | |
| 500 | CH₂CH=CH₂ | 6-CF₃ | OCH₃ | |
| 501 | CH₂C≡CH | 6-F | OCH₃ | |
| 502 | CH₂CH=CHCH₃ | 6-OCF₂H | OCH₃ | |

TABLE 3

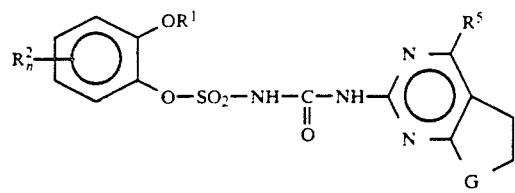

| Ex. No. | R¹ | R² | R⁵ | G | n | m.p. [°C.] |
|---|---|---|---|---|---|---|
| 503 | CH₂CH=CH₂ | H | CH₃ | CH₂ | 0 | |
| 504 | " | H | H | CH₂ | 0 | |
| 505 | " | H | OCH₃ | CH₂ | 0 | |
| 506 | CH₂CH₂Cl | H | CH₃ | O | 0 | |
| 507 | CH₂CH₂OCH₃ | H | CH₃ | CH₂ | 0 | |
| 508 | CH₂C≡CH | H | CH₃ | O | 0 | |
| 509 | CH₂C₆H₅ | H | CH₃ | CH₂ | 0 | |
| 510 | CH₂CH=CHCl | H | CH₃ | O | 0 | |
| 511 | CH₂CH=CHCH₃ | H | CH₃ | CH₂ | 0 | |
| 512 | CH₂CH₂Br | H | CH₃ | O | 0 | |
| 513 | CH₂C≡CCH₃ | H | CH₃ | CH₂ | 0 | |
| 514 | C₅H₉ | H | CH₃ | O | 0 | |
| 515 | CH₂CH=CH₂ | 6-CH₃ | CH₃ | CH₂ | 1 | |
| 516 | CH₂CH₂Cl | 6-OCH₃ | CH₃ | O | 1 | |
| 517 | CH₂CH₂OCH₃ | 6-Cl | CH₃ | CH₂ | 1 | |
| 518 | CH₂CH=CH₂ | 6-CF₃ | CH₃ | CH₂ | 1 | |
| 519 | CH₂C≡CH | 6-F | CH₃ | CH₂ | 1 | |
| 520 | CH₂CH=CHCH₃ | 6-OCF₂H | CH₃ | O | 1 | |

TABLE 4

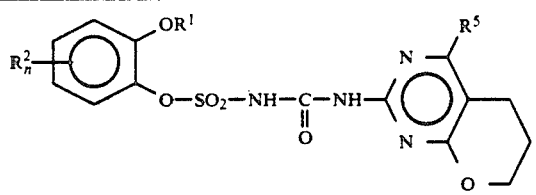

| Ex. No. | R¹ | R² | R⁵ | n | m.p. |
|---|---|---|---|---|---|
| 521 | CH₂CH=CH₂ | H | CH₃ | 0 | |
| 522 | " | H | H | 0 | |
| 523 | " | H | OCH₃ | 0 | |
| 524 | CH₂CH₂Cl | H | CH₃ | 0 | |
| 525 | CH₂CH₂OCH₃ | H | CH₃ | 0 | |
| 526 | CH₂C≡CH | H | CH₃ | 0 | |
| 527 | CH₂C₆H₅ | H | CH₃ | 0 | |
| 528 | CH₂CH=CHCl | H | CH₃ | 0 | |
| 529 | CH₂CH=CHCH₃ | H | CH₃ | 0 | |
| 530 | CH₂CH₂Br | H | CH₃ | 0 | |
| 531 | CH₂C≡CCH₃ | H | CH₃ | 0 | |

TABLE 4-continued

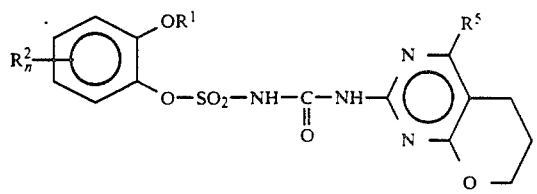

| Ex. No. | R¹ | R² | R⁵ | n | m.p. |
|---|---|---|---|---|---|
| 532 | C₅H₉ | H | CH₃ | 0 | |
| 533 | CH₂CH=CH₂ | 6-CH₃ | CH₃ | 1 | |
| 534 | CH₂CH₂Cl | 6-OCH₃ | CH₃ | 1 | |
| 535 | CH₂CH₂OCH₃ | 6-Cl | CH₃ | 1 | |
| 536 | CH₂CH=CH | 6-F | CH₃ | 1 | |
| 537 | CH₂C≡CH | 6-F | CH₃ | 1 | |
| 538 | CH₂CH=CHCH₃ | 6-OCF₂H | CH₃ | 1 | |

TABLE 5

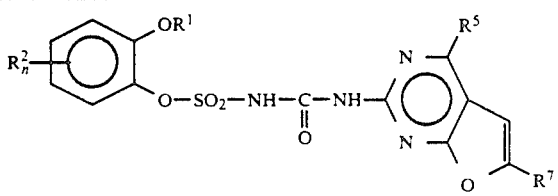

| Ex. No. | R¹ | R² | R⁵ | R⁷ | n | m.p. |
|---|---|---|---|---|---|---|
| 539 | CH₂CH=CH₂ | H | CH₃ | CH₃ | 0 | |
| 540 | " | H | H | CH₃ | 0 | |
| 541 | " | H | OCH₃ | CH₃ | 0 | |
| 542 | CH₂CH₂Cl | H | CH₃ | CH₃ | 0 | |
| 543 | CH₂CH₂OCH₃ | H | CH₃ | H | 0 | |
| 544 | CH₂C≡CH | H | CH₃ | CH₃ | 0 | |
| 545 | CH₂C₆H₅ | H | CH₃ | H | 0 | |
| 546 | CH₂CH=CHCl | H | CH₃ | CH₃ | 0 | |
| 547 | CH₂CH=CHCH₃ | H | CH₃ | H | 0 | |
| 548 | CH₂CH₂Br | H | CH₃ | CH₃ | 0 | |
| 549 | CH₂C≡CCH₃ | H | CH₃ | H | 0 | |
| 550 | C₅H₉ | H | CH₃ | CH₃ | 0 | |
| 551 | CH₂CH=CH₂ | 6-CH₃ | CH₃ | H | 1 | |
| 552 | CH₂CH₂Cl | 6-OCH₃ | CH₃ | CH₃ | 1 | |
| 553 | CH₂CH₂OCH₃ | 6-Cl | CH₃ | H | 1 | |
| 554 | CH₂CH=CH₂ | 6-CF₃ | CH₃ | CH₃ | 1 | |
| 555 | CH₂C≡CH | 6-F | CH₃ | H | 1 | |
| 556 | CH₂CH=CHCH₃ | 6-OCF₂H | CH₃ | CH₃ | 1 | |

TABLE 6

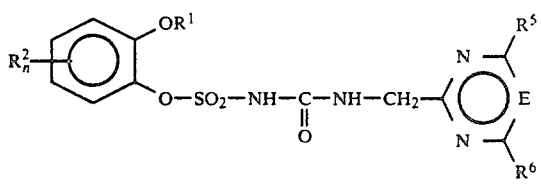

| Ex. No. | R¹ | R² | R⁵ | R⁶ | E | n | m.p. |
|---|---|---|---|---|---|---|---|
| 557 | CH₂CH=CH₂ | H | OCH₃ | OCH₃ | CH | 0 | |
| 558 | " | H | OCH₃ | CH₃ | CH | 0 | |
| 559 | " | H | OCH₃ | CH₃ | N | 0 | |
| 560 | CH₂CH₂Cl | H | OCH₃ | CH₃ | CH | 0 | |
| 561 | CH₂CH₂OCH₃ | H | OCH₃ | CH₃ | N | 0 | |
| 562 | CH₂C≡CH | H | OCH₃ | OCH₃ | CH | 0 | |
| 563 | CH₂C₆H₅ | H | OCH₃ | CH₃ | N | 0 | |
| 564 | CH₂CH=CHCl | H | OCH₃ | CH₃ | CH | 0 | |
| 565 | CH₂CH=CHCH₃ | H | OCH₃ | OCH₃ | N | 0 | |
| 566 | CH₂CH₂Br | H | OCH₃ | CH₃ | CH | 0 | |
| 567 | CH₂C≡CCH₃ | H | OCH₃ | CH₃ | N | 0 | |
| 568 | C₅H₉ | H | OCH₃ | OCH₃ | CH | 0 | |
| 569 | CH₂CH=CH₂ | 6-CH₃ | OCH₃ | CH₃ | N | 1 | |
| 570 | CH₂CH₂Cl | 6-OCH₃ | OCH₃ | CH₃ | CH | 1 | |

TABLE 6-continued

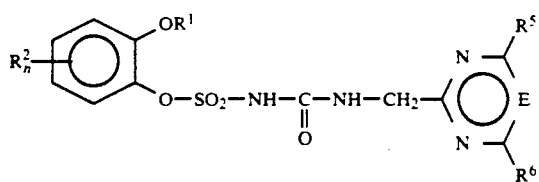

| Ex. No. | $R^1$ | $R^2$ | $R^5$ | $R^6$ | E | n | m.p. |
|---|---|---|---|---|---|---|---|
| 571 | CH$_2$CH$_2$OCH$_3$ | 6-Cl | OCH$_3$ | OCH$_3$ | N | 1 | |
| 572 | CH$_2$CH=CH$_2$ | 6-CF$_3$ | OCH$_3$ | CH$_3$ | CH | 1 | |
| 573 | CH$_2$C≡CH | 6-F | OCH$_3$ | OCH$_3$ | N | 1 | |
| 574 | CH$_2$CH=CHCH$_3$ | 6-OCF$_2$H | OCH$_3$ | CH$_3$ | CH | 1 | |

TABLE 7

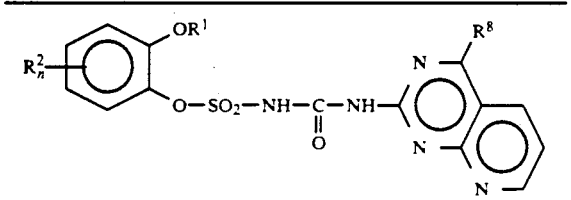

| Ex. No. | $R^1$ | $R^2$ | $R^8$ | n | m.p. |
|---|---|---|---|---|---|
| 575 | CH$_2$CH=CH$_2$ | H | OCH$_3$ | 0 | |
| 576 | " | H | CH$_3$ | 0 | |
| 577 | " | 3-Cl | CH$_3$ | 0 | |
| 578 | CH$_2$CH$_2$Cl | H | CH$_3$ | 0 | |
| 579 | CH$_2$CH$_2$OCH$_3$ | H | CH$_3$ | 0 | |
| 580 | CH$_2$C≡CH | H | OCH$_3$ | 0 | |
| 581 | CH$_2$CH=CHCl | H | CH$_3$ | 0 | |
| 582 | CH$_2$CH=CHCl | H | CH$_3$ | 0 | |
| 583 | CH$_2$CH=CHCH$_3$ | H | OCH$_3$ | 0 | |
| 584 | CH$_2$CH$_2$Br | H | CH$_3$ | 0 | |
| 585 | CH$_2$C≡CCH$_3$ | H | CH$_3$ | 0 | |
| 586 | C$_5$H$_{11}$ | H | OCH$_3$ | 0 | |
| 587 | CH$_2$CH=CH$_2$ | 6-CH$_3$ | CH$_3$ | 1 | |
| 588 | CH$_2$CH$_2$Cl | 6-OCH$_3$ | CH$_3$ | 1 | |
| 589 | CH$_2$CH$_2$OCH$_3$ | 6-Cl | OCH$_3$ | 1 | |
| 590 | CH$_2$CH=CH$_2$ | 6-CF$_3$ | CH$_3$ | 1 | |
| 591 | CH$_2$C≡CH | 6-F | OCH$_3$ | 1 | |
| 592 | CH$_2$CH=CHCH$_3$ | 6-OCF$_2$H | CH$_3$ | 1 | |

TABLE 8

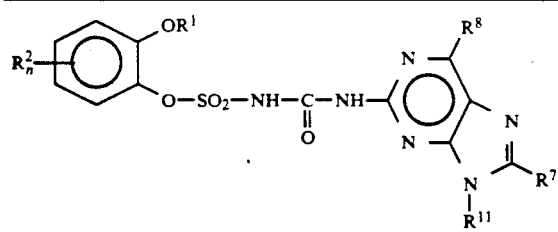

| Ex. No. | $R^1$ | $R^2$ | $R^7$ | $R^8$ | $R^{11}$ | n | m.p. |
|---|---|---|---|---|---|---|---|
| 593 | CH$_2$CH=CH$_2$ | H | H | OCH$_3$ | H | 0 | |
| 594 | " | H | H | CH$_3$ | CH$_3$ | 0 | |
| 595 | " | H | CH$_3$ | CH$_3$ | CH$_3$ | 0 | |
| 596 | CH$_2$CH$_2$Cl | H | H | CH$_3$ | H | 0 | |
| 597 | CH$_2$CH$_2$OCH$_3$ | H | H | CH$_3$ | CH$_3$ | 0 | |
| 598 | CH$_2$C≡CH | H | CH$_3$ | OCH$_3$ | CHF$_2$ | 0 | |
| 599 | CH$_2$C$_6$H$_5$ | H | H | CH$_3$ | H | 0 | |
| 600 | CH$_2$CH=CHCl | H | H | CH$_3$ | CH$_3$ | 0 | |
| 601 | CH$_2$CH=CHCH$_3$ | H | CH$_3$ | OCH$_3$ | CH$_3$ | 0 | |
| 602 | CH$_2$CH$_2$Br | H | H | CH$_3$ | H | 0 | |
| 603 | CH$_2$C≡CCH$_3$ | H | H | CH$_3$ | CH$_2$CF$_3$ | 0 | |
| 604 | C$_5$H$_9$ | H | CH$_3$ | OCH$_3$ | CH$_3$ | 0 | |
| 605 | CH$_2$CH=CH$_2$ | 6-CH$_3$ | H | CH$_3$ | H | 1 | |
| 606 | CH$_2$CH$_2$Cl | 6-OCH3 | H | CH$_3$ | CH$_3$ | 1 | |

TABLE 8-continued

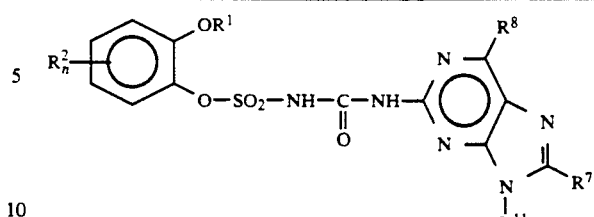

| Ex. No. | $R^1$ | $R^2$ | $R^7$ | $R^8$ | $R^{11}$ | n | m.p. |
|---|---|---|---|---|---|---|---|
| 607 | CH$_2$CH$_2$OCH$_3$ | 6-Cl | CH$_3$ | OCH$_3$ | CH$_3$ | 1 | |
| 608 | CH$_2$CH=CH$_2$ | 6-CF$_3$ | H | CH$_3$ | H | 1 | |
| 609 | CH$_2$C≡CH | 6-F | H | OCH$_3$ | CH$_3$ | 1 | |
| 610 | CH$_2$CH=CHCH$_3$ | 6-Cl | CH$_3$ | CH$_3$ | CH$_3$ | 1 | |

BIOLOGICAL EXAMPLES

The damage on the weed plants and the tolerance by crop plants were scored using a key where numbers from 0 to 5 express the activity. In this key
0 denotes no action
1 denotes 0–20% action or damage
2 denotes 20–40% action or damage
3 denotes 40–60% action or damage
4 denotes 60–80% action or damage
5 denotes 80–100% action or damage

1. Pre-emergence action on weeds

Seeds or rhizome pieces of monocotyledon and dicotyledon weed plants were placed in plastic pots containing sandy loam soil and covered with soil. Various dosages of aqueous suspensions or emulsions of the compounds according to the invention formulated as wettable powders or emulsion concentrates were then applied to the surface of the cover soil, at an application rate of water of 600–800 l/ha (converted).

After the treatment, the pots were placed in the greenhouse and maintained at good growth conditions for the weeds. Visual scoring of the damage to plants or the emergence damage was carried out after the emergence of the test plants after a trial period of 3 to 4 weeks, comparing them to untreated control plants. As shown by the score data in Table 9, the compounds according to the invention have good herbicidal pre-emergence activity against a broad range of weed grasses and broad-leaf weeds.

2. Post-emergence action on weeds

Seeds or rhizome pieces of monocotyledon and dicotyledon weeds were placed in plastic pots in sandy loam ground, covered with soil and grown in the greenhouse under good growth conditions. Three weeks after sowing, the test plants were treated in the three-leaf stage.

Various dosages of the compounds according to the invention formulated as wettable powders or emulsion concentrates were sprayed onto the green parts of the plants, at an application rate of water of 600–800 l/ha (converted), and the action of the preparations was scored visually after the test plants had remained in the greenhouse for about 3 to 4 weeks under optimum growth conditions, comparing them to untreated control plants.

The agents according to the invention exhibit a good herbicidal activity against a broad range of economically important weed grasses and broad-leaf weeds, also in the post-emergence treatment (Table 10).

3. Tolerance by crop plants

In further greenhouse experiments, seeds of a relatively large number of crop plants and weeds were placed in sandy loam ground and covered with soil.

Some of the pots were treated immediately as described under 1., those remaining were placed in the greenhouse until the plants had developed two to three true leaves and were then sprayed with various dosages of the substances according to the invention as described under 2.

Four to five weeks after application, with the plants remaining in the greenhouse, visual scoring revealed that the compounds according to the invention did not cause any damage to dicotyledonous crops, such as, for example, soya, cotton, rape, sugar beet and potatoes when applied both as a pre-emergence and post-emergence treatment, even at high dosages of active substance. Furthermore, Gramineae crops such as, for example, barley, wheat, rye, sorghum millets, maize or rice, were also unaffected by some of the substances. Thus, the compounds of the formula I exhibit high selectivity on application for controlling undersired plant growth in agricultural crops.

TABLE 9

Pre-emergence action of the compounds according to the invention

| Ex. No. No. | Dosage in kg of a.i./ha | herbicidal action | | | | | |
|---|---|---|---|---|---|---|---|
| | | SIA | CRS | STM | AS | ECG | LOM |
| 2 | 0.6 | 5 | 5 | 5 | 1 | 4 | 3 |
| 3 | 0.6 | 5 | 5 | 5 | 2 | 5 | 2 |
| 4 | 0.6 | 5 | 5 | 5 | 1 | 3 | 2 |
| 71 | 0.6 | 5 | 5 | 3 | 3 | 4 | 4 |
| 74 | 0.6 | 5 | 5 | 4 | 1 | 3 | 1 |
| 84 | 0.6 | 5 | 5 | 5 | 1 | 3 | 1 |

TABLE 10

Post-emergence action of the compounds according to the invention

| Ex. No. No. | Dosage in kg of a.i./ha | herbicidal action | | | | | |
|---|---|---|---|---|---|---|---|
| | | SIA | CRS | STM | AS | ECG | LOM |
| 2 | 0.6 | 5 | 5 | 5 | 1 | 4 | 1 |
| 3 | 0.6 | 5 | 5 | 5 | 1 | 4 | 2 |
| 4 | 0.6 | 5 | 4 | 4 | 1 | 4 | 2 |
| 71 | 0.6 | 5 | 4 | 4 | 3 | 4 | 3 |
| 74 | 0.6 | 5 | 5 | 5 | 1 | 3 | 2 |
| 84 | 0.6 | 5 | 5 | 5 | 0 | 5 | 3 |

Abbreviations:
SIA = *Sinapis alba*
CRS = *Chrysanthemum segetum*
STM = *Stellaria media*
AS = *Avena sativa*
ECG = *Echinochloa crus-galli*
LOM = *Lolium multiflorum*
a.i. = active substance

We claim:

1. A compound of formula I or a salt thereof $$\text{R}^2_n\text{-}\underset{\text{O-SO}_2\text{-NH-}\underset{\underset{\text{Y}}{\|}}{\text{C}}\text{-}\underset{\underset{\text{R}^3}{|}}{\text{N}}\text{-R}^4}{\overset{\text{OR}^1}{\bigcirc}}$$ (I)

where $R^1$ is
($C_2$–$C_8$)alkenyl;
($C_2$–$C_8$)alkynyl;
($C_1$–$C_8$)alkyl, ($C_2$–$C_8$)alkenyl or ($C_2$–$C_8$)alkynyl, each of which is monosubstituted or polysubstituted by chloro or monosubstituted or disubstituted by ($C_1$–$C_6$)alkoxy, ($C_2$–$C_6$)alkenyloxy, ($C_2$–$C_6$)alkynyloxy, ($C_1$–$C_6$)alkylthio, ($C_1$–$C_6$)alkylsulfinyl, ($C_1$–$C_6$)alkysulfonyl, ($C_1$–$C_6$)alkoxycarbonyl, $NO_2$, CN or by phenyl;
($C_3$–$C_8$)cycloalkyl which can be monosubstituted or polysubstituted by halogen or monosubstituted or disubstituted by ($C_1$–$C_4$)alkoxy or ($C_1$–$C_4$)alkylthio;
($C_5$–$C_8$)cycloalkenyl, cyclopropylmethyl or epoxypropyl;
furfuryl, tetrahydrofurfuryl or phenoxy-($C_1$–$C_4$)alkyl, each of which can be substituted by halogen, ($C_1$–$C_4$)alkyl or ($C_1$–$C_4$)alkoxy; or
phenyl which can be monosubstituted or polysubstituted by halogen, ($C_1$–$C_4$)alkyl, ($C_1$–$C_4$)alkoxy, $NO_2$, $CF_3$, CN or $OCHF_2$;
or in the event that $R^2$ is ($C_2$–$C_8$)alkenyl, ($C_2$–$C_8$)alkynyl, phenyl or phenoxy, each of which can be substituted as indicated below, or $R^2$ is ($C_1$–$C_4$)alkylsulfonyl or ($C_1$–$C_4$)alkylsulfinyl, and further $n \neq 0$, then $R^1$ can also be ($C_1$–$C_8$)alkyl;
$R^2$ is, each independently of any other $R_2$ when $n > 1$, ($C_1$–$C_8$)alkyl, ($C_2$–$C_8$)alkenyl, ($C_2$–$C_8$)alkynyl, phenyl, phenoxy, ($C_1$–$C_4$)alkoxy, ($C_1$–$C_4$)alkylthio, ($C_1$–$C_4$)alkoxycarbonyl, ($C_2$–$C_4$)alkenyloxycarbonyl or ($C_2$–$C_4$)alkynyloxycarbonyl, each of which can be monosubstituted or polysubstituted by halogen or monosubstituted or disubstituted by ($C_1$–$C_4$)alkoxy or ($C_1$–$C_4$)alkylthio; or
is halogen, $NO_2$, ($C_1$–$C_4$)alkylsulfonyl or ($C_1$–$C_4$)alkylsulfinyl;
n is 0, 1, 2 or 3;
Y is O or S;
$R^3$ is hydrogen, ($C_1$–$C_8$)alkyl, ($C_2$–$C_8$)alkenyl, ($C_3$–$C_8$)-alkynyl or ($C_1$–$C_4$)alkoxy;
$R^4$ is a heterocyclic radical of formula $$\underset{N}{\overset{N}{\bigcirc}}\underset{R^6}{\overset{R^5}{\diagup}} \quad \text{or} \quad -CH_2-\underset{N}{\overset{N}{\bigcirc}}\underset{R^6}{\overset{R^5}{\diagup}};$$

$R^5$ and $R^6$, independently of one another, are hydrogen or halogen;
($C_1$–$C_6$)alkyl, ($C_1$–$C_6$)alkoxy or ($C_1$–$C_6$)alkylthio, each of which can be monosubstituted or polysubstituted by halogen or monosubstituted or disubstituted by ($C_1$–$C_4$)alkoxy or ($C_1$–$C_4$)alkylthio;
or are a radical of the formula $-NR^{12}R^{13}$, $-OCHR^7-CO_2R^{12}$, ($C_3$–$C_6$)cycloalkyl, ($C_3$–$C_5$)alkenyl, ($C_2$–$C_5$)alkynyl, ($C_3$–$C_5$)alkenyloxy or ($C_3$–$C_5$)alkynyloxy;
$R^7$ is hydrogen or ($C_1$–$C_4$)alkyl; and
$R^{12}$ and $R^{13}$, independently of one another, are hydrogen, ($C_1$–$C_4$)alkyl, ($C_2$–$C_4$)alkenyl or ($C_3$–$C_4$)alkynyl.

2. A compound of formula I or a salt thereof

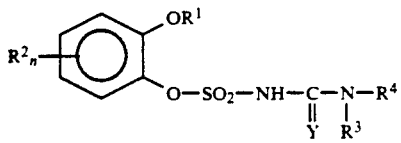

where R¹ is
- (C₂–C₈)alkenyl;
- (C₂–C₈)alkynyl;
- (C₁–C₈)alkyl, (C₂–C₈)alkenyl or (C₂–C₈)alkynyl, each of which is monosubstituted or disubstituted by (C₁–C₆)alkoxy, (C₂–C₆)alkenyloxy, (C₂–C₆)alkynyloxy, (C₁–C₆)alkylthio, (C₁–C₆)alkylsulfinyl, (C₁–C₆)alkylsulfonyl, (C₁–C₆)alkoxycarbonyl, NO₂, CN or by phenyl;
- (C₃–C₈)cycloalkyl which can be monosubstituted or polysubstituted by halogen or monosubstituted or disubstituted by (C₁–C₄)alkoxy or (C₁–C₄)alkylthio;
- (C₅–C₈)cycloalkenyl, cyclopropylmethyl or epoxypropyl;
- furfuryl, tetrahydrofurfuryl or phenoxy-(C₁–C₄)alkyl, each of which can be substituted by halogen, (C₁–C₄)alkyl or (C₁–C₄)alkoxy; or phenyl which can be monosubstituted or polysubstituted by halogen, (C₁–C₄)alkyl, (C₁–C₄)alkoxy, NO₂, CF₃, CN or OCHF₂;
- or in the event that R² is (C₂–C₈)alkenyl, (C₂–C₈)alkynyl, phenyl or phenoxy, each of which can be substituted as indicated below, or R² is (C₁–C₄)alkylsulfonyl or (C₁–C₄)alkylsulfinyl, and further n≠0, then R¹ can also be (C₁–C₈)alkyl;

R² is, each independently of any other R₂ when n>1, (C₁–C₈)alkyl, (C₂–C₈)alkenyl, (C₂–C₈)alkynyl, phenyl, phenoxy, (C₁–C₄)alkoxy, (C₁–C₄)alkylthio, (C₁–C₄)alkoxycarbonyl, (C₂–C₄)alkenyloxycarbonyl or (C₂–C₄)alkynyloxycarbonyl, each of which can be monosubstituted or polysubstituted by halogen or monosubstituted or disubstituted by (C₁–C₄)alkoxy or (C₁–C₄)alkylthio; or is halogen, NO₂, (C₁–C₄)alkylsulfonyl or (C₁–C₄)alkylsulfinyl;

n is 0, 1, 2 or 3;

Y is O or S;

R³ is hydrogen, (C₁–C₈)alkyl, (C₂–C₈)alkenyl, (C₃–C₈)-alkynyl or (C₁–C₄)alkoxy;

R⁴ is a heterocyclic radical of formula

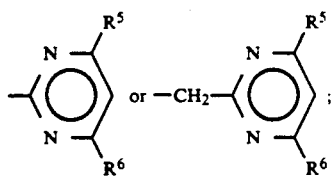

R⁵ and R⁶, independently of one another, are hydrogen or halogen;
(C₁–C₆)alkyl, (C₁–C₆)alkoxy or (C₁–C₆)alkylthio, each of which can be monosubstituted or polysubstituted by halogen or monosubstituted or disubstituted by (C₁–C₄)alkoxy or (C₁–C₄)alkylthio;
or are a radical of the formula —NR¹²R¹³, —OCH R⁷—CO₂R¹², (C₃–C₆)cycloalkyl, (C₃–C₅)alkenyl, (C₂–C₄)alkynyl, (C₃–C₅)alkenyloxy or (C₃–C₅)alkynyloxy;

R⁷ is hydrogen or (C₁–C₄)alkyl; and
R¹² and R¹³, independently of one another, are hydrogen, (C₁–C₄)alkyl, (C₂–C₄)alkenyl or (C₃–C₄)alkynyl.

3. A compound of formula I or a salt thereof

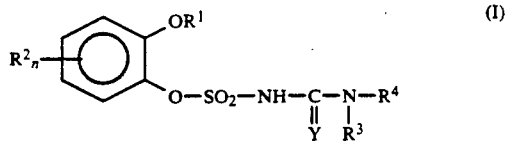

where R¹ is
- (C₂–C₈)alkenyl;
- (C₂–C₈)alkynyl;
- (C₁–C₈)alkyl, (C₂–C₈)alkenyl or (C₂–C₈)alkynyl, each of which is monosubstituted or polysubstituted by chloro or bromo or monosubstituted or disubstituted by (C₁–C₆)alkoxy, (C₂–C₆)alkenyloxy, (C₂–C₆)-alkynyloxy, (C₁–C₆)alkylthio, (C₁–C₆)alkylsulfinyl, (C₁–C₆)alkylsulfonyl, (C₁–C₆)alkoxycarbonyl, NO₂, CN or by phenyl;
- (C₃–C₈)cycloalkyl which can be monosubstituted or polysubstituted by halogen or monosubstituted or disubstituted by (C₁–C₄)alkoxy or (C₁–C₄)alkylthio;
- (C₅–C₈)cycloalkenyl, cyclopropylmethyl or epoxypropyl;
- furfuryl, tetrahydrofurfuryl or phenoxy-(C₁–C₄)alkyl, each of which can be substituted by halogen, (C₁–C₄)alkyl or (C₁–C₄)alkoxy; or
- phenyl which can be monosubstituted or polysubstituted by halogen, (C₁–C₄)alkyl, (C₁–C₄)alkoxy, NO₂, CF₃, CN or OCHF₂;
- or in the event that R² is (C₂–C₈)alkenyl, (C₂–C₈)-alkynyl, phenyl or phenoxy, each of which can be substituted as indicated below, or R² is (C₁–C₄)alkylsulfonyl or (C₁–C₄)alkylsulfinyl, and further n≠0, then R¹ can also be (C₁–C₈)alkyl;

R² is, each independently of any other R₂ when n>1, (C₁–C₈)alkyl, (C₂–C₈)alkenyl, (C₂–C₈)alkynyl, phenyl, phenoxy, (C₁–C₄)alkoxy, (C₁–C₄)alkylthio, (C₁–C₄)-alkoxycarbonyl, (C₂–C₄)alkenyloxycarbonyl or (C₂–C₄)-alkynyloxycarbonyl, each of which can be monosubstituted or polysubstituted by halogen or monosubstituted or disubstituted by (C₁–C₄)alkoxy or (C₁–C₄)alkylthio; or is halogen, NO₂, (C₁–C₄)alkylsulfonyl or (C₁–C₄)alkylsulfinyl;

n is 0, 1, 2 or 3;

Y is O or S;

R³ is hydrogen, (C₁–C₈)alkyl, (C₂–C₈)alkenyl, (C₃–C₈)-alkynyl or (C₁–C₄)alkoxy;

R⁴ is a heterocyclic radical of formula

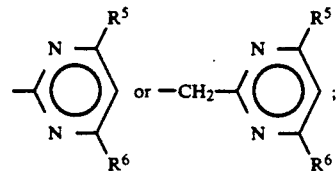

R⁵ and R⁶, independently of one another, are hydrogen or halogen;
(C₁–C₆)alkyl, (C₁–C₆)alkoxy or (C₁–C₆)alkylthio, each of which can be monosubstituted or polysubstituted by halogen or monosubstituted or disubstituted by (C₁-C₄)alkoxy or (C₁-C₄)alkylthio; or are a radical of the formula —NR¹²R¹³, —OCHR⁷—CO₂R¹², (C₃-C₆)cycloalkyl, (C₃-C₅)alkenyl, (C₂-C₄)alkynyl, (C₃-C₅)alkenyloxy or (C₃-C₅)alkynyloxy;

R⁷ is hydrogen or (C₁-C₄)alkyl; and

R¹² and R¹³, independently of one another, are hydrogen, (C₁-C₄)alkyl, (C₂-C₄)alkenyl or (C₃-C₄)alkynyl.

4. A compound of the formula I of claim 3 or a salt thereof, where R¹ is (C₁-C₄)alkyl, (C₂-C₅)alkenyl or (C₂-C₄)alkynyl, each of which is monosubstituted or polysubstituted by chloro or bromo or monosubstituted or disubstituted by (C₁-C₆)alkoxy, (C₂-C₆)alkenyloxy, (C₂-C₆)-alkynyloxy, (C₁-C₆)alkylthio, (C₁-C₆)alkylsulfinyl, (C₁-C₆)alkylsulfonyl, (C₁-C₆)alkoxycarbonyl, NO₂, CN or by phenyl, or (C₂-C₅)alkenyl or (C₂-C₄)alkynyl or, in the event that n=1 and R² is (C₂-C₈)alkenyl or (C₂-C₈)alkynyl, then R¹ can also be (C₁-C₄)alkyl;

R² is (C₁-C₄)alkyl, (C₂-C₅)alkenyl, (C₂-C₄)alkynyl, (C₁-C₄)alkoxycarbonyl, phenyl, phenoxy, (C₁-C₄)alkoxy, (C₁-C₄)alkylthio, each of which can be monosubstituted or polysubstitued by halogen or monosubstituted or disubstituted by (C₁-C₄)alkoxy or (C₁-C₄)alkythio, or is halogen;

n is 0, 1 or 2;

Y is O;

R³ is hydrogen, (C₁-C₄)alkyl or (C₃-C₄)alkenyl;

R⁴ is a heterocyclic radical of the formula

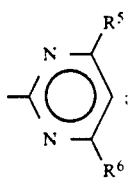

R⁵ and R⁶ independently of one another are halogen, or (C₁-C₄)alkyl, (C₁-C₄)alkoxy or (C₁-C₄)alkylthio, each of which can be monosubstituted or poly substituted by halogen or monosubstituted or disubstituted by (C₁-C₄)alkoxy or (C₁-C₄)alkylthio.

5. A compound of the formula I of claim 3 or a salt thereof, where R¹ is (C₁-C₄)alkyl, (C₂-C₅)alkenyl, or (C₂-C₄)alkynyl, each of which is monosubstituted or polysubstituted by chloro or bromo or monosubstituted or disubstituted by (C₁-C₆)alkoxy, (C₂-C₆)alkenyloxy, (C₂-C₆)-alkynyloxy, (C₁-C₆)alkylthio, (C₁-C₆)alkylsulfinyl, (C₁-C₆)alkylsulfonyl, (C₁-C₆)alkoxycarbonyl, NO₂, CN or by phenyl, or (C₂-C₅)alkenyl or (C₂-C₄)alkynyl;

R² is (C₁-C₄)alkyl, (C₂-C₅)alkenyl, (C₁-C₄)alkoxycarbonyl, (C₁-C₄)alkoxy or (C₁-C₄)alkylthio, each of which can be monosubstituted or polysubstituted by halogen or monosubstituted or disubstituted by (C₁-C₄)alkoxy or (C₁-C₄)alkythio), or is fluorine or chlorine, n=0 or 1, R³ is hydrogen or methyl, R⁴ is a heterocyclic radical of the formula

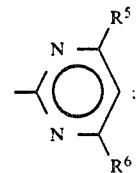

and

R⁵ and R⁶ independently of one another are chlorine, bromine, (C₁-C₄)alkyl, (C₁-C₄)alkoxy, OCHF₂, OCH₂CF₃ or CF₃.

6. A herbicidal composition containing an effective herbicidal amount of one or more compounds of the formula I or salts thereof as claimed in claim 3 and inert auxiliaries.

7. A plant growth-regulating composition containing an effective plant-growth regulating amount of one or more compounds of the formula I or salts thereof as claimed in claim 3 and inert auxiliaries.

8. A method of controlling weed plants, which comprises applying an effective amount of one or more compounds of the formula I or salts thereof, as claimed in claim 3, to these weed plants or the soil used for agriculture or industry.

9. A method of regulating the growth of crop plants which comprises applying an effective amount of one or more compounds of the formula I or salts thereof, as claimed in claim 3, to these crop plants or the cropped area.

10. 1-[2-(2-chloroethoxy)phenoxysulfonyl]-3-(4,6-dimethoxypyrimidin-2-yl)urea.

11. 3-(4,6-dimethoxypyrimidin-2-yl)-1-(2-propargyloxyphenoxysulfonyl)urea.

12. 3-(4,6-dimethoxypyrimidin-2-yl)-1-[2-(2-methoxyethoxy)-phenoxysulfonyl]urea.

13. A compound of formula I, as claimed in claim 3, wherein R¹ is CH₂CH₂OCH₃, R³ is H, R⁴ is

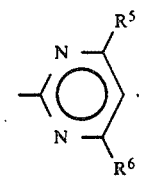

R⁵ is CH₃, R⁶ is CH₃, n is 0 and Y is O.

14. A compound of formula I, as claimed in claim 3, wherein
R¹ is CH₂CH=CH₂, R³ is H, R⁴ is

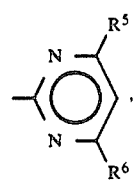

R⁵ is CH₃, R⁶ is CH₃, n is 0 and Y is O.

15. A compound of formula I, as claimed in claim 3, wherein R¹ is CH₂CH=CH₂, R³ is H, R⁴ is

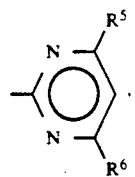
$R^5$ is $OCH_3$, $R^6$ is $CH_3$, n is 0 and Y is O.
16. A compound of formula I, as claimed in claim 3, wherein $R^1$ is $CH_2CH=CH_2$, $R^3$ is H, $R^4$ is
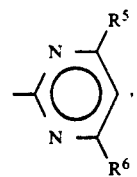
$R^5$ is $OCH_3$, $R^6$ is $OCH_3$, n is 0 and Y is O.
* * * * *